(12) United States Patent
Ramos Clamote et al.

(10) Patent No.: US 8,864,810 B2
(45) Date of Patent: Oct. 21, 2014

(54) DEVICE FOR IMPLANTING A VASCULAR PROSTHESIS

(75) Inventors: Joachim Ramos Clamote, Nice (FR); Yves Alimi, Nice (FR); Vincent Garitey, Nice (FR)

(73) Assignees: Universite d'Aix-Marseille, Marseilles (FR), part interest; Assistance Publique-Hopitaux de Marseille, Marseilles (FR), part interest (*) Notice: Subject to any disclaimer, the term of this patent is extended or adjusted under 35 U.S.C. 154(b) by 175 days.

(21) Appl. No.: 12/744,162

(22) PCT Filed: Nov. 21, 2008

(86) PCT No.: PCT/EP2008/065957
§ 371 (c)(1),
(2), (4) Date: May 21, 2010

(87) PCT Pub. No.: WO2009/065917
PCT Pub. Date: May 28, 2009

(65) Prior Publication Data
US 2010/0249895 A1 Sep. 30, 2010

(30) Foreign Application Priority Data
Nov. 23, 2007 (FR) ................................. 07 59269

(51) Int. Cl.
| | | |
|---|---|---|
| *A61F 2/06* | (2013.01) | |
| *A61M 25/06* | (2006.01) | |
| *A61F 2/958* | (2013.01) | |
| *A61M 25/10* | (2013.01) | |
| *A61F 2/95* | (2013.01) | |
| *A61F 2/91* | (2013.01) | |

(52) U.S. Cl.
CPC ................. *A61F 2/064* (2013.01); *A61F 2/958* (2013.01); *A61M 25/1002* (2013.01); *A61M 25/0662* (2013.01); *A61F 2/95* (2013.01); *A61F 2/91* (2013.01)
USPC ......................................... 623/1.11; 606/192

(58) Field of Classification Search
CPC ............ A61F 2/95; A61F 2/954; A61F 2/958; A61M 25/0062; A61M 25/0068; A61M 25/007; A61M 25/0102
USPC .................... 623/1.11–1.12, 1.23, 1.27, 1.35; 606/191–198
See application file for complete search history.

(56) References Cited

U.S. PATENT DOCUMENTS

| | | | |
|---|---|---|---|
| 4,983,166 A | | 1/1991 | Yamawaki |
| 5,928,192 A | * | 7/1999 | Maahs ........................ 604/96.01 |

(Continued)

FOREIGN PATENT DOCUMENTS

| | | |
|---|---|---|
| WO | 99/13808 | 3/1999 |
| WO | 00/66007 | 11/2000 |

(Continued)

OTHER PUBLICATIONS

Elastic Properties and Young Modulus for some Materials, The Engineering Toolbox, www.engineeringtoolbox.com/young-modulus-d_417.html.*
Information Disclosure Statement dated Feb. 3, 2009, from corresponding PCT application.

*Primary Examiner* — Darwin Erezo
*Assistant Examiner* — Kendra Obu
(74) *Attorney, Agent, or Firm* — Young & Thompson

(57) ABSTRACT

Implantation device for implanting a prosthesis (110) in a vessel (1), including a balloon (128) and a dilation catheter (120) for supplying fluid to the balloon (128), the dilation catheter (120) having a proximal end, a distal end (124) and a distal part designed to be introduced into the vessel (1), characterized in that the distal part includes a bend (123) and also an upstream portion (121) and a downstream portion (122) that are contiguous to the bend and that are arranged between the bend and, respectively, the proximal end and the distal end (124).

20 Claims, 24 Drawing Sheets

(56) References Cited

U.S. PATENT DOCUMENTS

Figure 1:
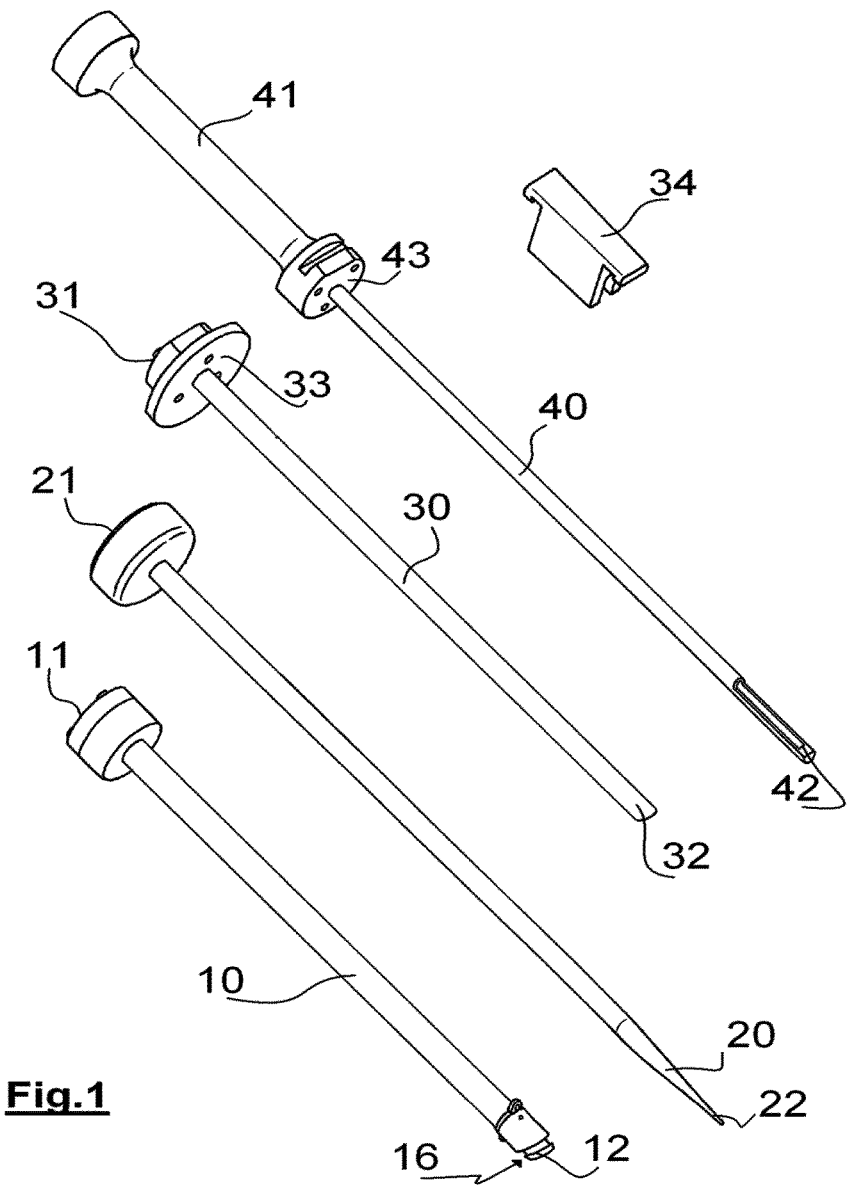

| | | | |
|---|---|---|---|
| 5,972,017 A | 10/1999 | Berg et al. | |
| 6,029,671 A * | 2/2000 | Stevens et al. | 128/898 |
| 6,692,483 B2 * | 2/2004 | Vardi et al. | 604/529 |
| 7,141,060 B1 * | 11/2006 | Metz et al. | 623/1.11 |
| 2001/0001114 A1 * | 5/2001 | Tsugita et al. | 604/96.01 |
| 2005/0192654 A1 * | 9/2005 | Chanduszko et al. | 607/116 |
| 2006/0052858 A1 * | 3/2006 | Wilson et al. | 623/1.11 |
| 2006/0247756 A1 * | 11/2006 | Richter | 623/1.11 |
| 2006/0265043 A1 * | 11/2006 | Mandrusov et al. | 623/1.11 |
| 2007/0016241 A1 | 1/2007 | Von Oepen et al. | |
| 2009/0171430 A1 * | 7/2009 | Baim et al. | 623/1.11 |

FOREIGN PATENT DOCUMENTS

| | | |
|---|---|---|
| WO | WO 0134061 A1 * | 5/2001 |
| WO | WO 2005053574 A2 * | 6/2005 |

\* cited by examiner

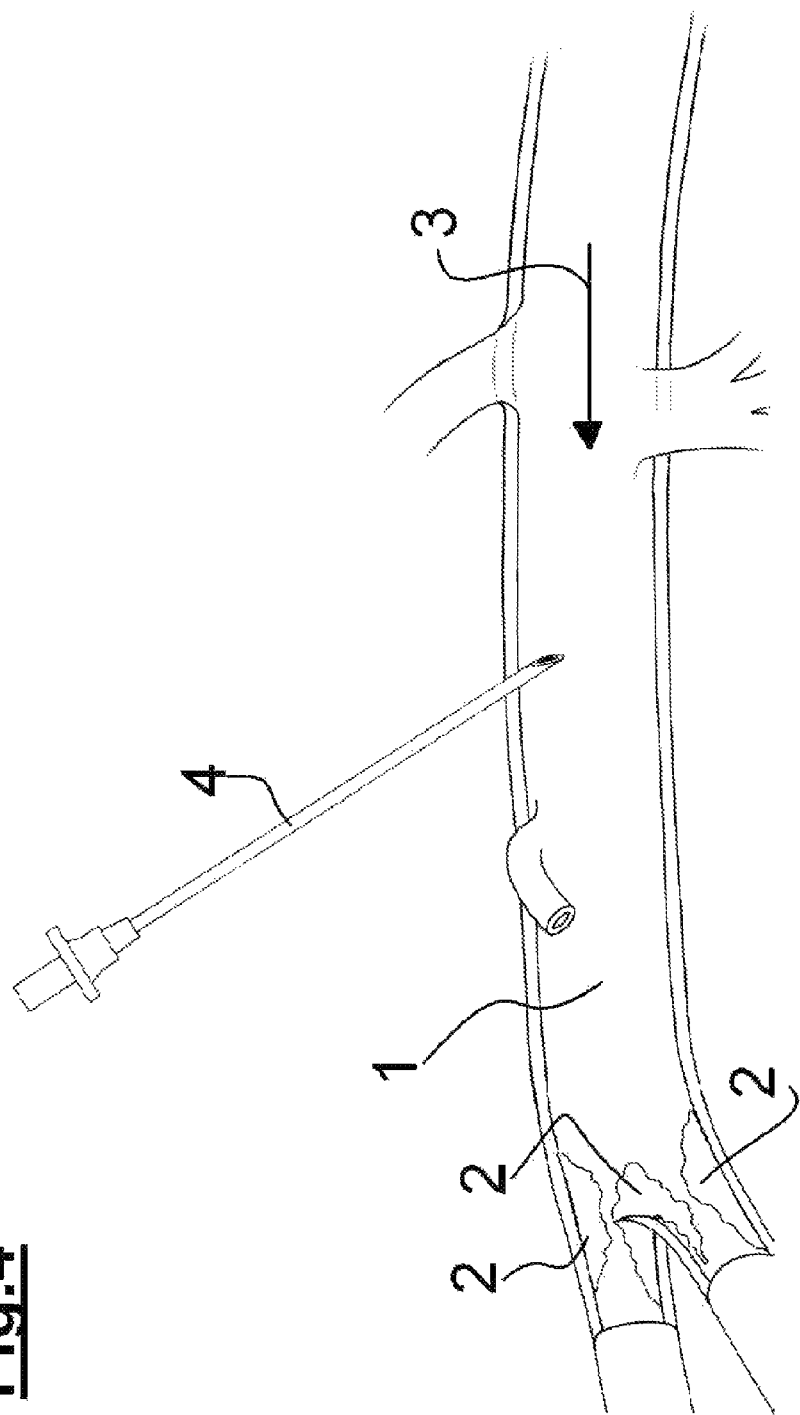

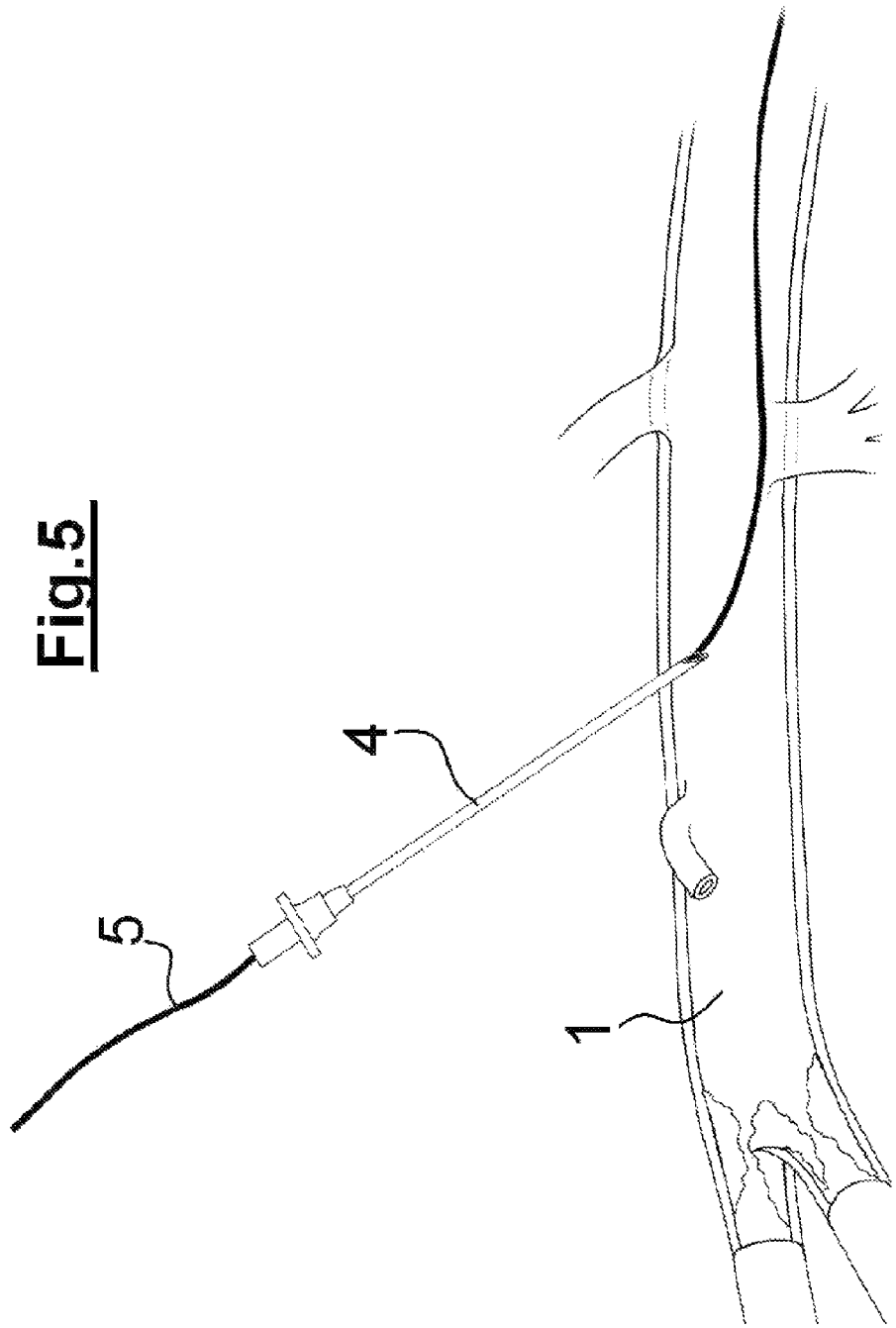

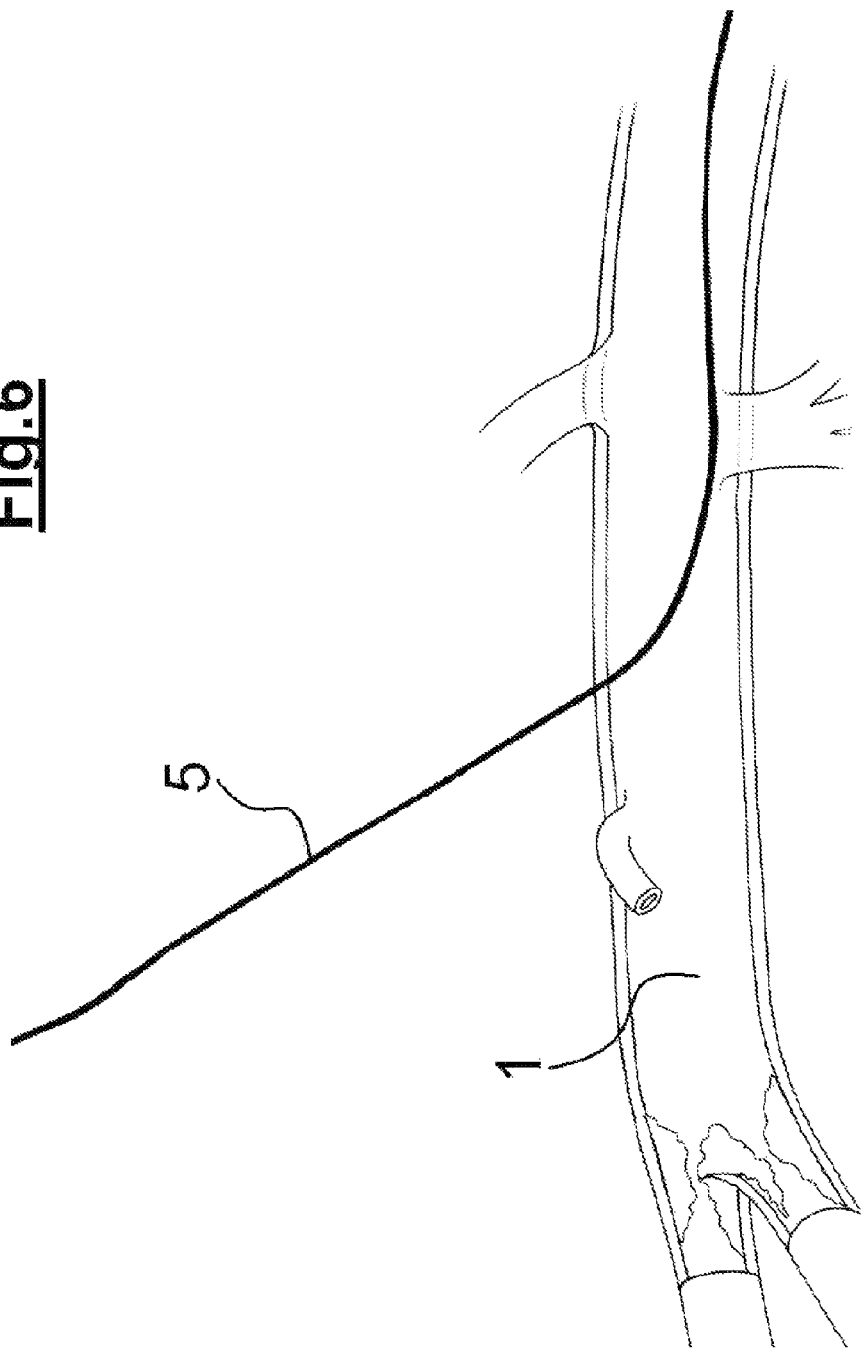

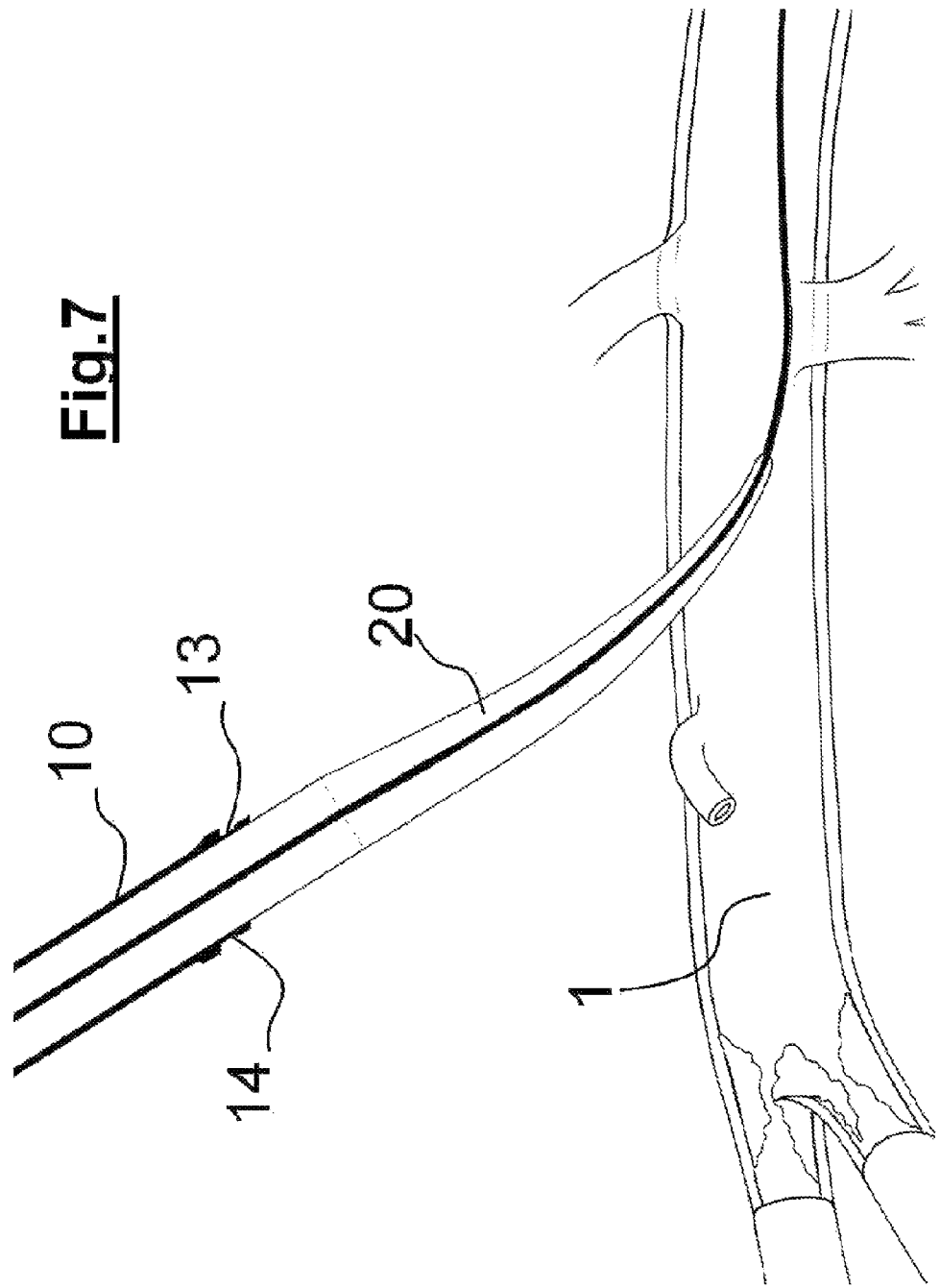

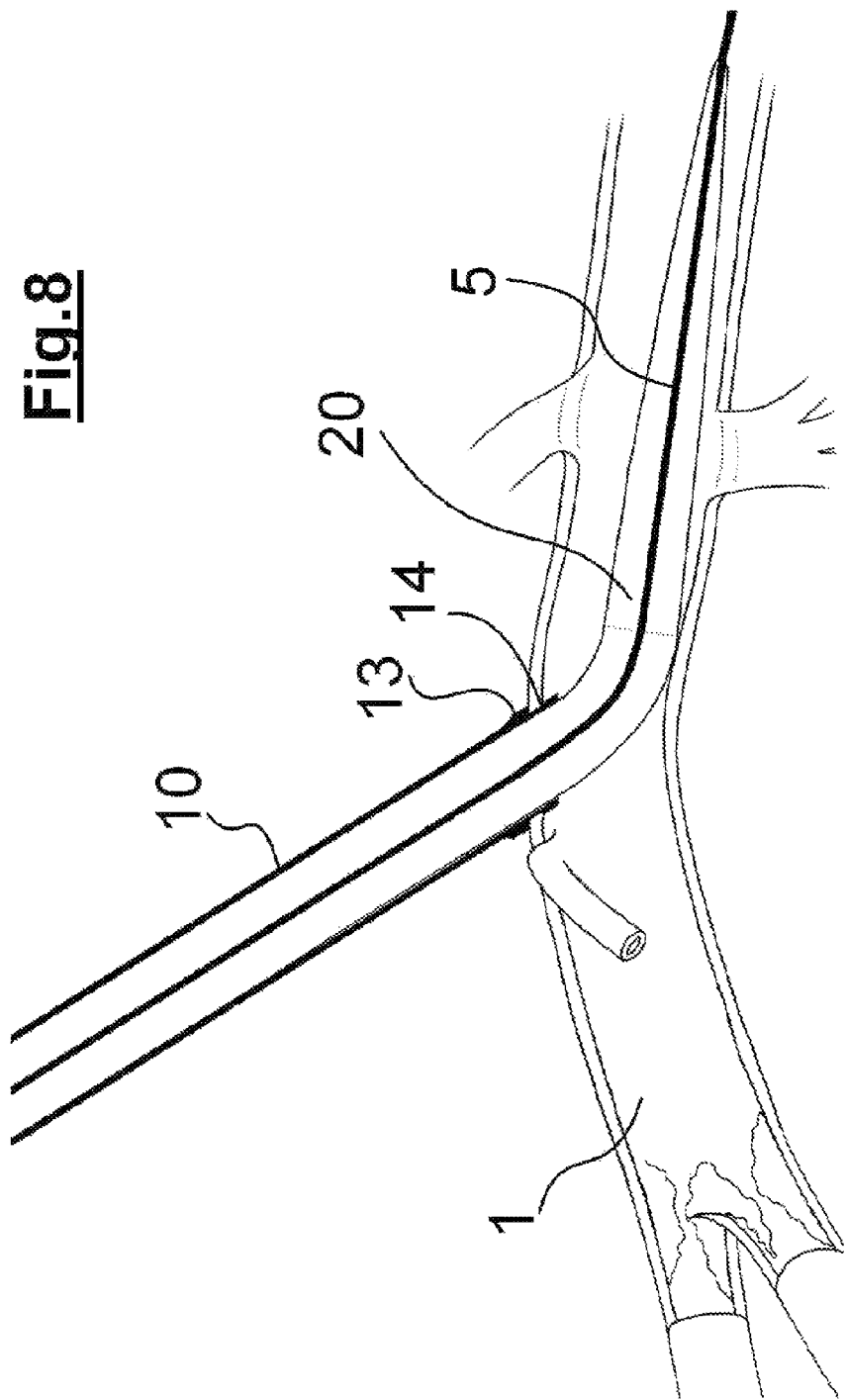

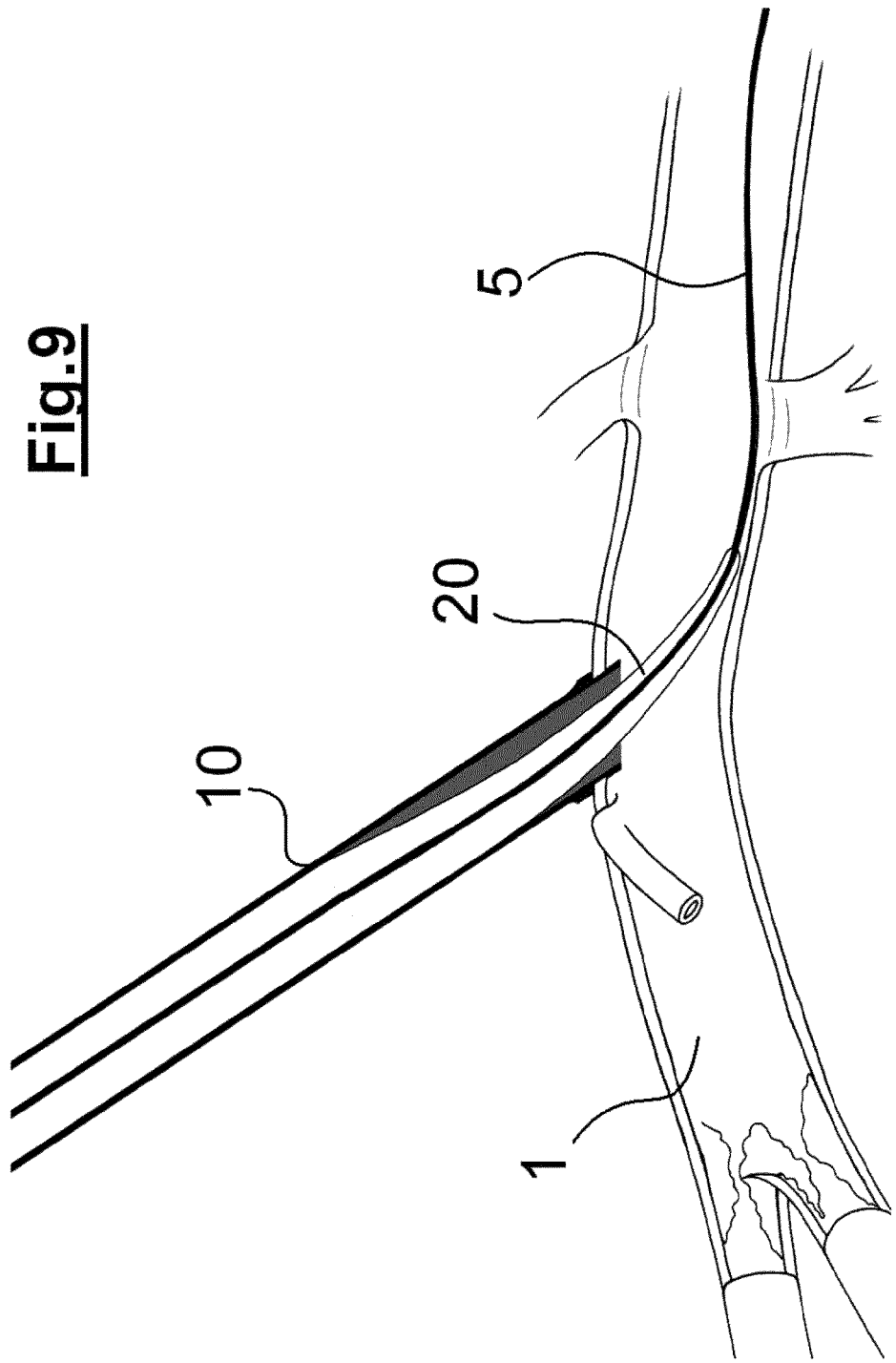

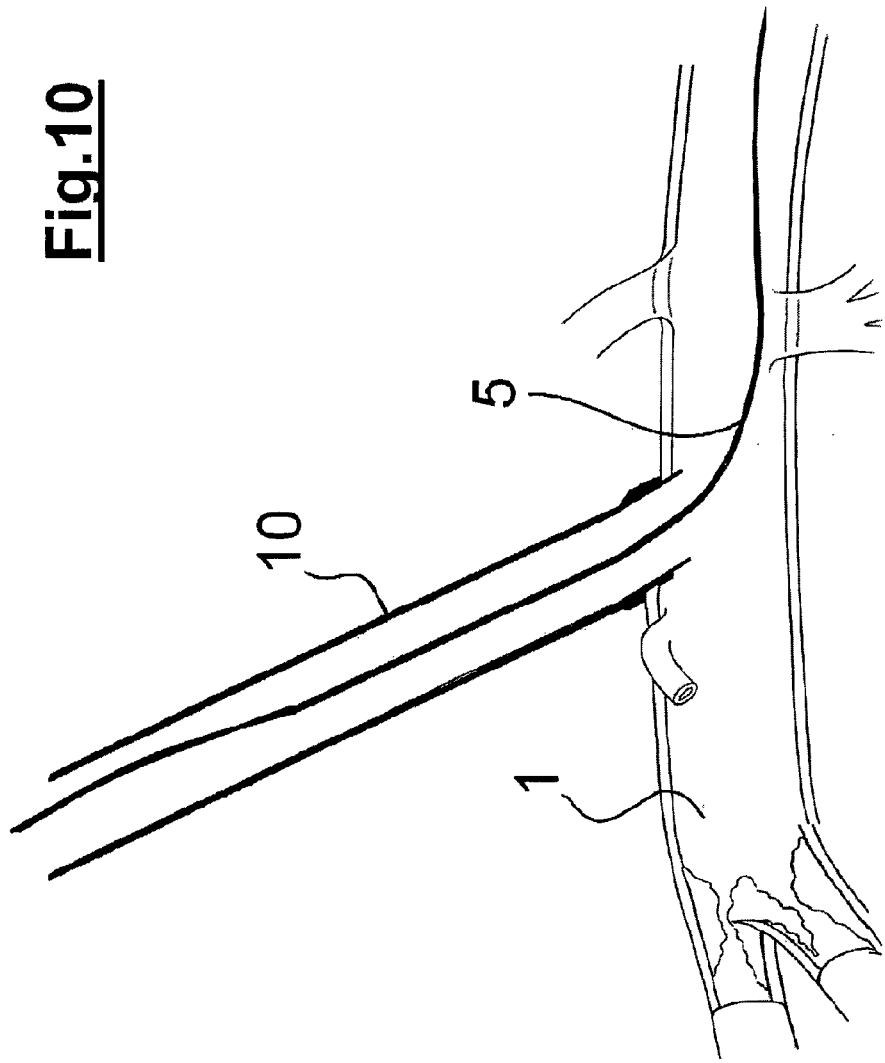

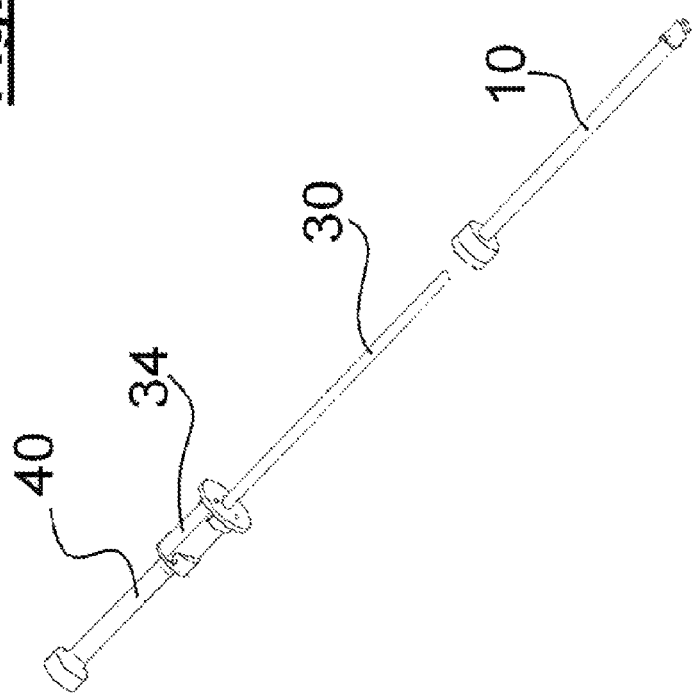

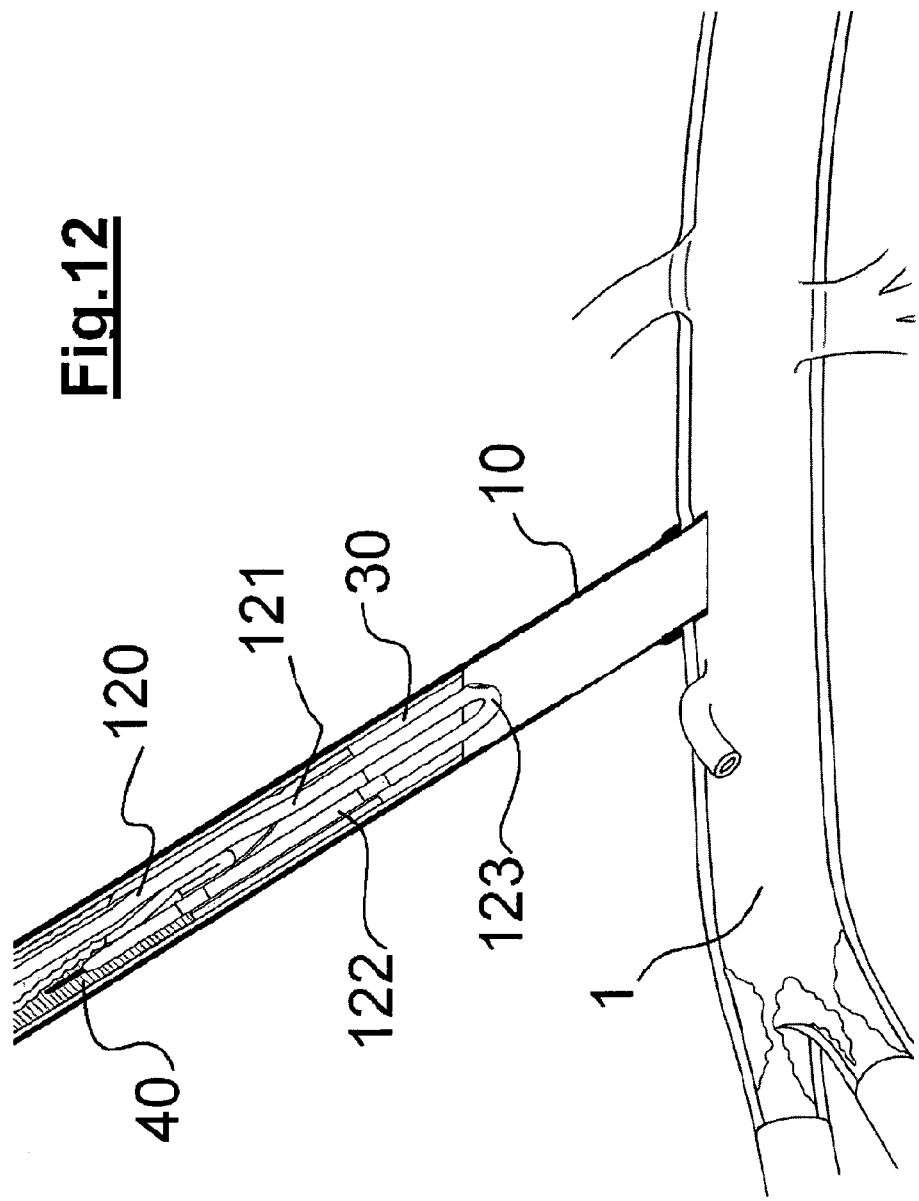

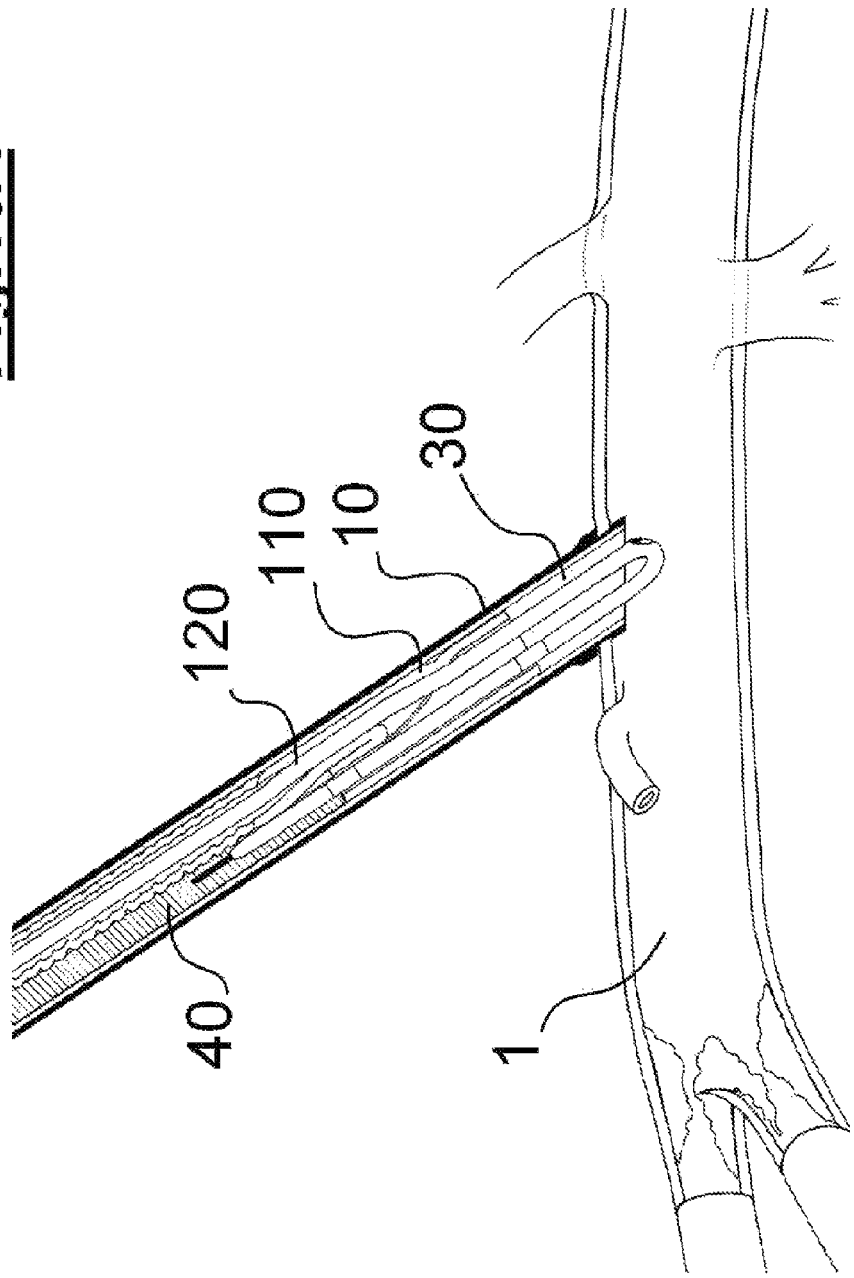

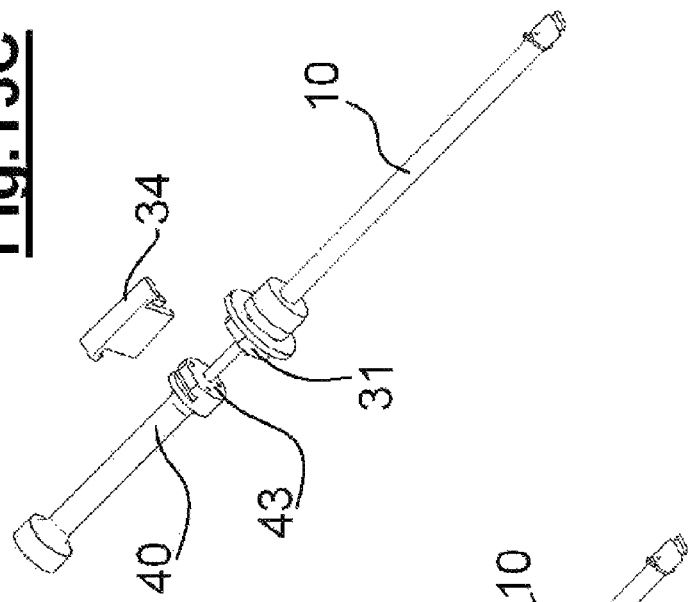
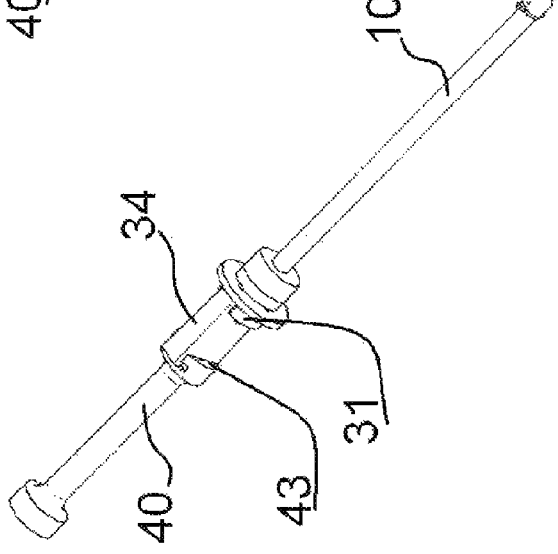

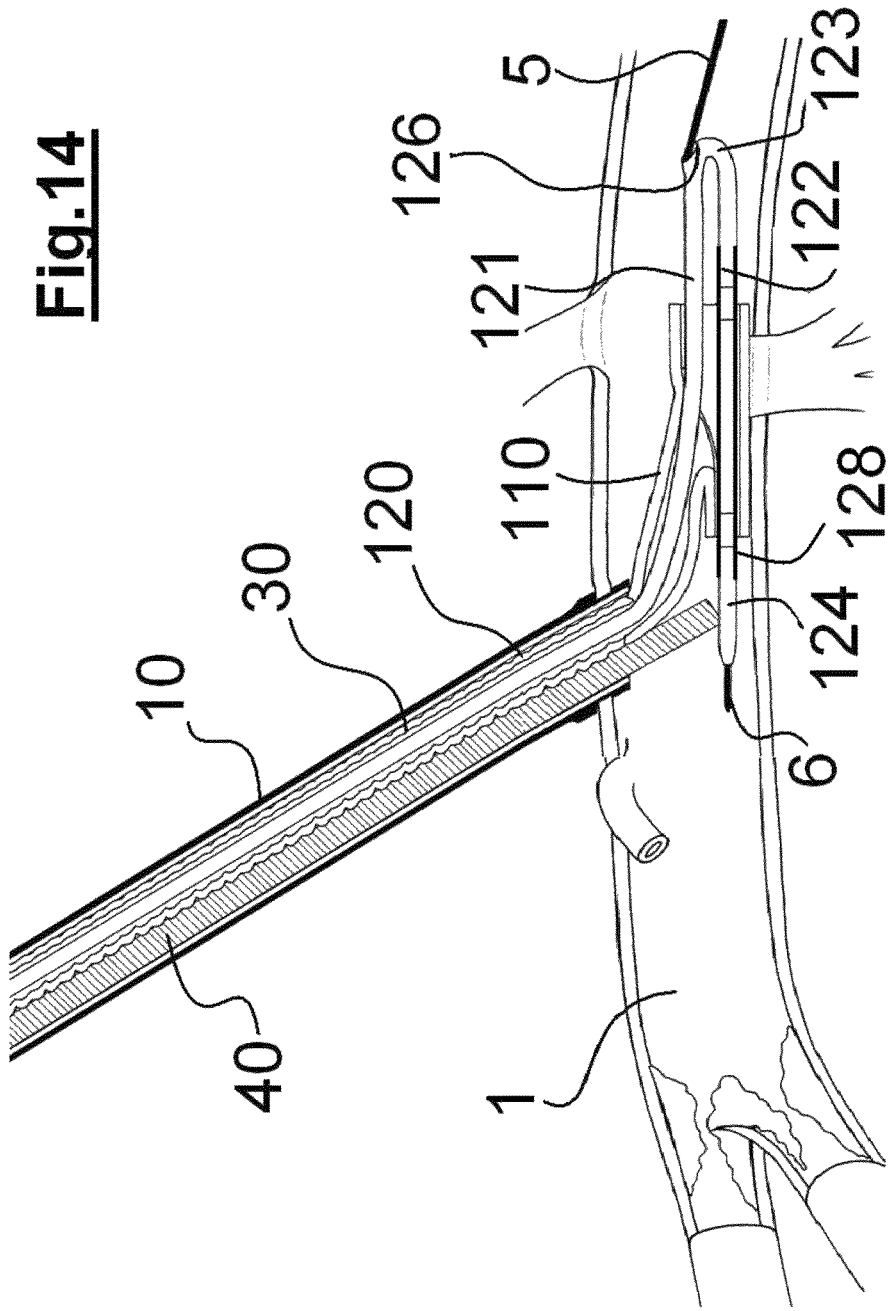

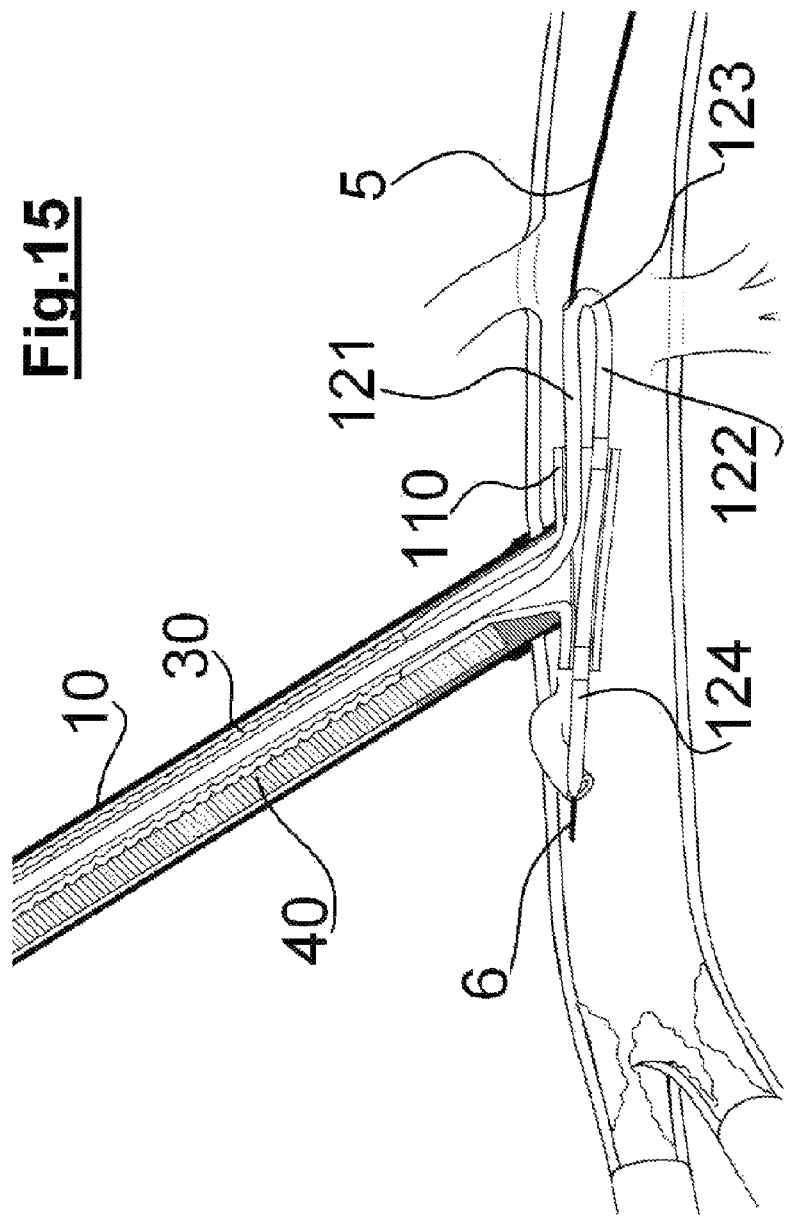

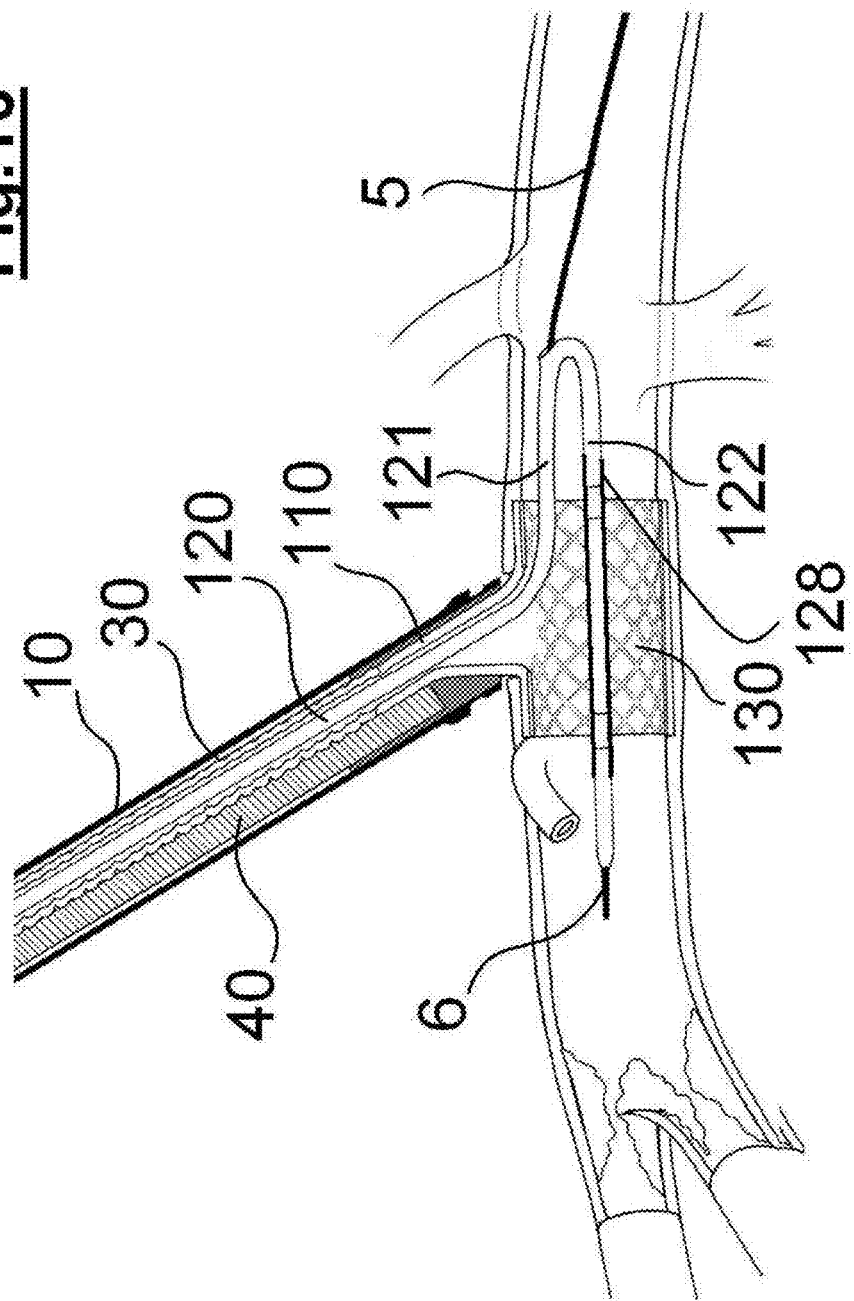

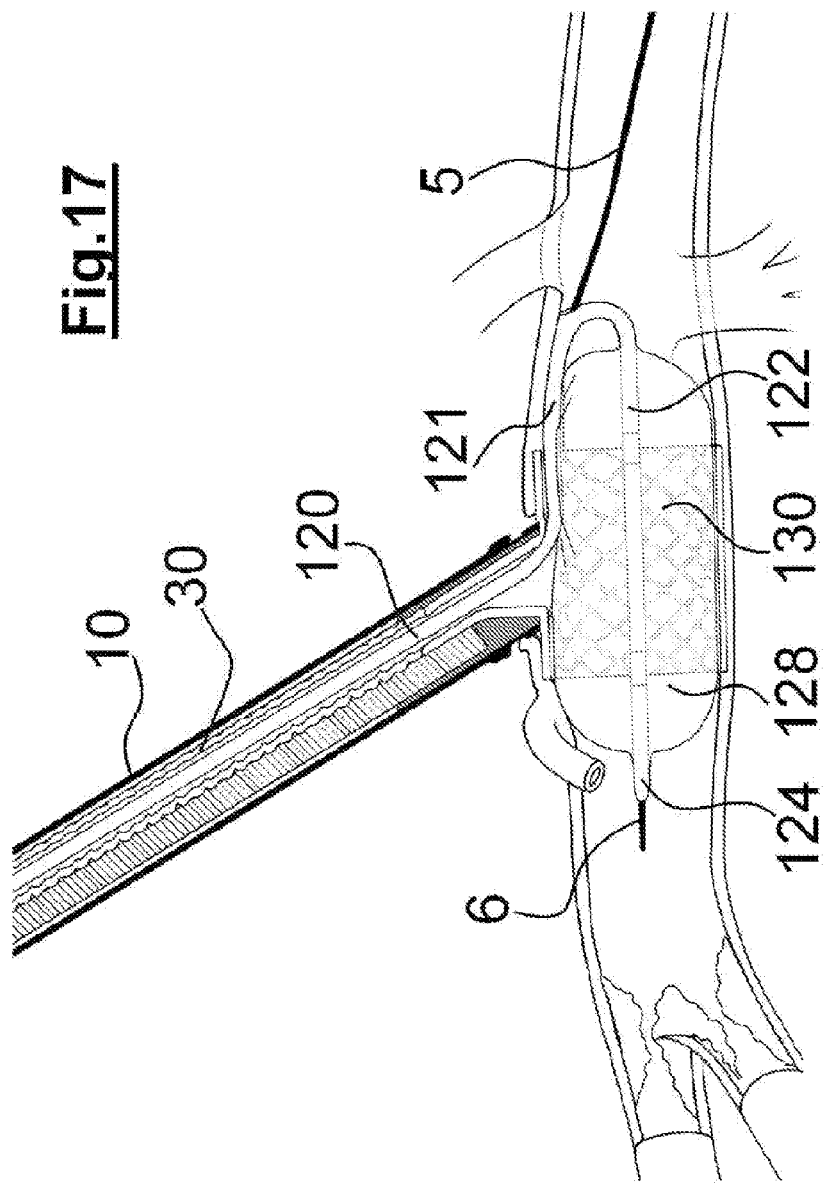

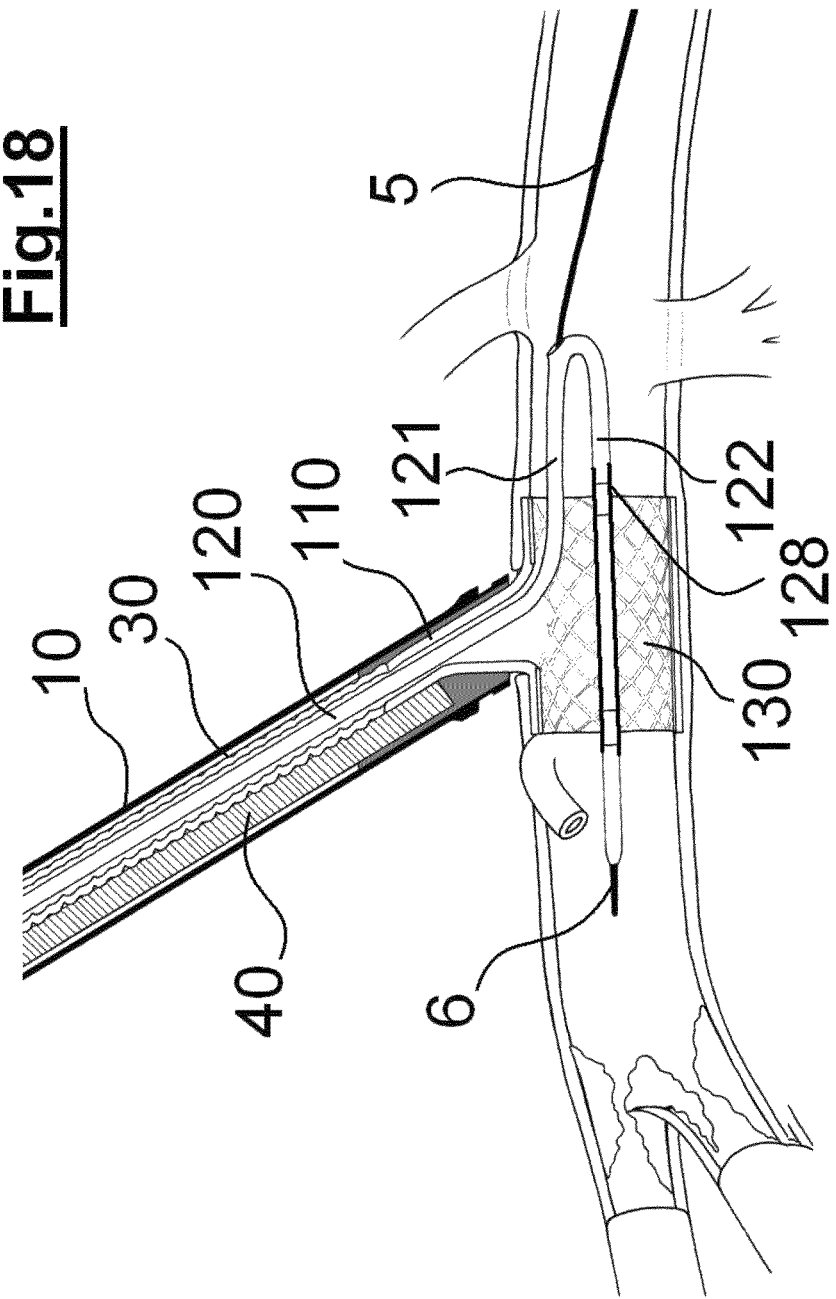

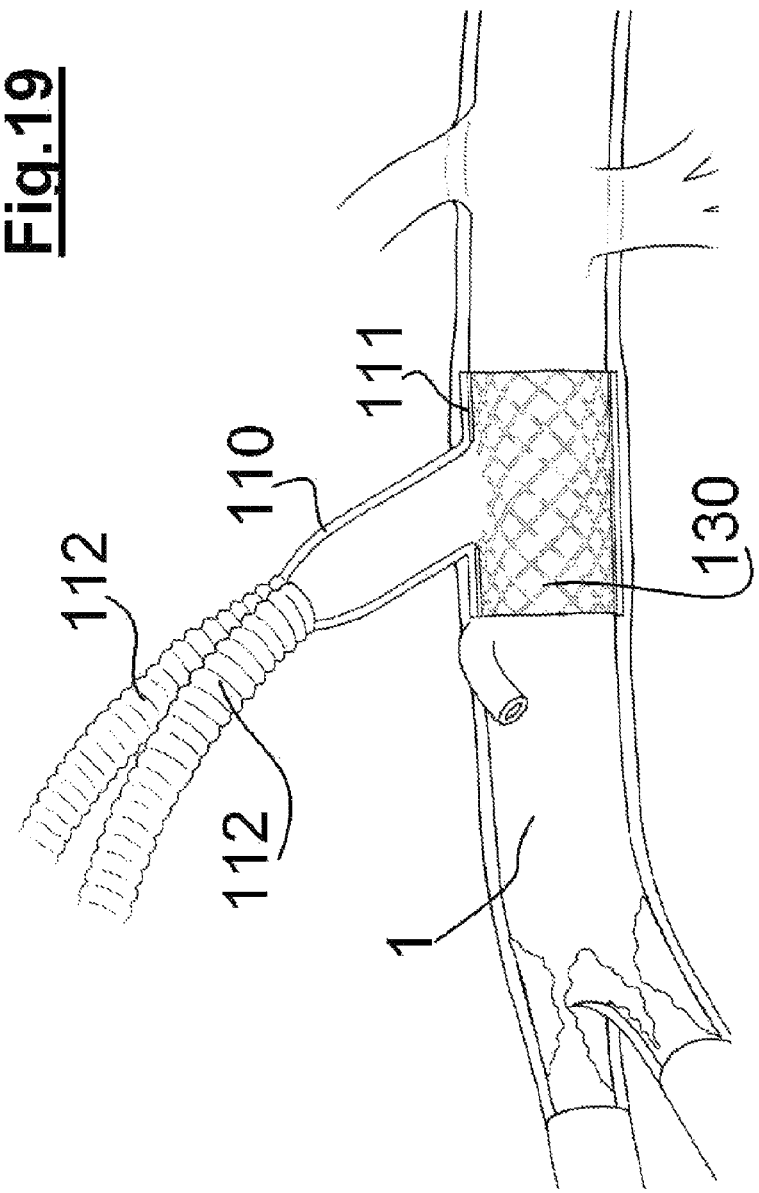

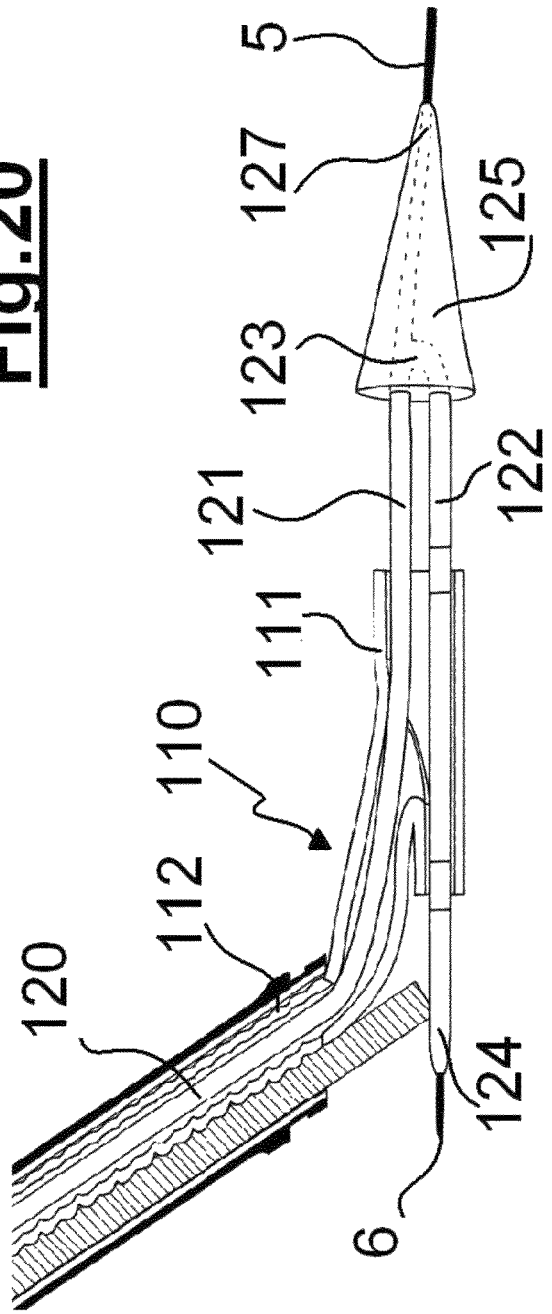

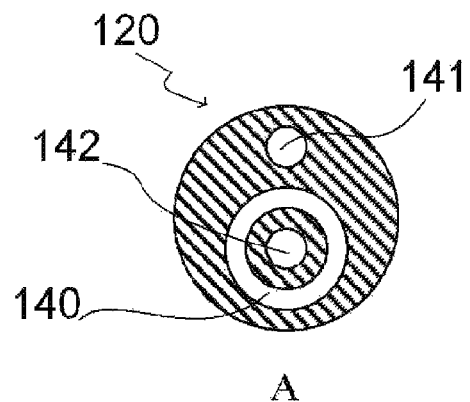
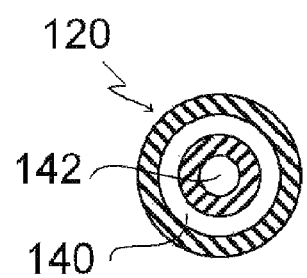
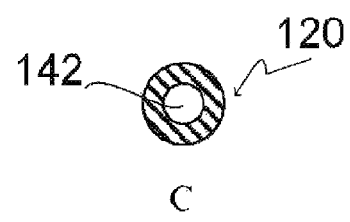
Fig. 26

DEVICE FOR IMPLANTING A VASCULAR PROSTHESIS

BACKGROUND OF THE INVENTION

The invention relates to a vascular prosthesis implantation device. More particularly, it relates to a dilation catheter associated with a balloon that enables a stent to press on a vascular prosthesis in a blood vessel. The invention will have an application mainly in the implanting of a vascular prosthesis perpendicular to a puncture in a vessel through which the prosthesis is inserted. Particularly advantageously, the invention will apply to bypasses or the closure of vascular access.

DISCUSSION OF PRIOR ART

Proceeding in a known manner, the vascular prosthesis is placed perpendicular to a transparietal puncture through which the prosthesis is inserted, positioning the prosthesis perpendicular to the puncture then deploying the stent contained in the prosthesis. A balloon supplied with fluid by a dilation catheter presses on the stent—vascular prosthesis assembly in the wall of the blood vessel.

Such prosthesis implants raise numerous difficulties. In particular the placement of the prosthesis compared to the blood vessel must be perfectly controlled. Moreover, the stability and seal of the connection between the prosthesis and the blood vessel must also be very accurately positioned. When the procedure is undertaken without clamping the blood vessel, the prosthesis is more difficult to position, notably because of blood flow. Moreover, in the absence of clamping, the introduction of the prosthesis, its placement and the seal of the connection must be done accurately, quickly and simply to avoid major, or even fatal, blood loss.

SUMMARY OF THE INVENTION

It would be particularly useful to have a device for the implanting of vascular prostheses that would improve the accuracy and/or simplicity and/or speed of known methods of implanting vascular prostheses.

To this end, the present invention refers to an implant device used to implant a prosthesis within a blood vessel, characterised in that it has a balloon and a dilation catheter to supply fluid to the balloon. The catheter includes a proximal end, distal end and a distal part designed to be introduced into the blood vessel, characterised in that the distal part includes an elbow or bend and an upstream portion and a downstream portion that are contiguous to the bend and located between the bend and, respectively, the proximal and distal ends, and in that the balloon is at least partially supported by the downstream portion.

Thus a device according to the invention makes it possible for a balloon to be positioned on its downstream portion before running in a direction more or less parallel to the longitudinal axis of the vessel. The balloon can easily take on the shape of the vessel's internal bend and it is sufficiently large to cover all the longitudinal dimensions of the stent positioned between the prosthesis and the balloon.

The specific shape of the dilation catheter allows for a wide choice of balloon dimensions and material. It also overcomes the usual constraints associated with implants positioned perpendicular to a puncture.

Moreover, the dilation catheter runs alongside the balloon and can even cross it from one side to the other. It ensures that the balloon remains correctly in place on the dilation catheter. This provides control of the placement and maintenance of the balloon by displacing the dilation catheter throughout the duration of the placement steps, before and after its dilation.

The implant device according to the invention improves the accuracy of the placement of the balloon of the stent and the vascular prosthesis during the implanting of the prosthesis perpendicular to the puncture.

It has been shown that the placement and maintenance of the prosthesis and stent within the blood vessel directly affect the seal and strength of the connection between prosthesis and blood vessel.

Thus an implant device according to the invention helps to significantly increase the quality of vascular prosthesis implants.

Moreover, an implant device according to the invention is simple to use. Such a device limits the duration and difficulty of known vascular prosthesis implant procedures.

An implant device according to the invention also allows for the insertion of a balloon, partly in its downstream and partly in its upstream portion. This variation considerably simplifies the action required to accurately position the balloon. It therefore helps to significantly reduce the duration and complexity of a prosthesis implant operation.

Optionally, an implant device according to the invention may have any of the following characteristics:
- the upper and downstream portions form an angle of between 0° and 30°.
- the elbow or bend is substantially U-shaped.
- the upstream and downstream portions are substantially parallel.
- the dilation catheter is elastic, notably at the level of the bend, to enable the upstream and downstream portions to be brought closer together or positioned wider apart.
- the dilation catheter includes an initial lumen between its proximal end and the bend.
- the first lumen is substantially rectilinear.
- the first lumen can receive an initial wire guide.
- the dilation catheter includes a second lumen between its proximal end and distal end, the second lumen being shaped to receive a second wire guide.
- the bend and/or the distal end of the dilation catheter has a cone-shaped or spherical tip extending the downstream portion.
- it includes a prosthesis and/or a stent into which is housed the balloon.

Moreover, according to the invention, the vascular prosthesis implant device comprises an implant device according to any of the above characteristics and an introduction catheter consisting of a proximal end and a distal end. The implant device is designed to slide from the proximal end to the distal end of the introduction catheter.

The implant system according to the invention may optionally have any of the following characteristics:
- the introduction catheter includes sealing and stabilization means fitted in such a way as to ensure a stable seal between the introduction catheter and the blood vessel.
- the sealing and stabilization means include a boss and a recess between the boss and the distal end of the introduction catheter,
- the sealing and stabilization means are elastic and fitted in such a way as to follow the sides of an approximately circular opening.
- the recess consists of an elastic material that follows the shape of the opening through the wall of the blood vessel.
- the sealing and stabilization means cannot be deformed or moved.

the distal end of the introduction catheter includes a bevelled edge or an external wall that flares out towards the proximal end of the introduction catheter.

it includes a delivery catheter and/or a pusher device fitted so as to slide the implant device from the proximal end of the introduction catheter to the distal end of the latter.

BRIEF DESCRIPTION OF THE INVENTION

Figure 3:
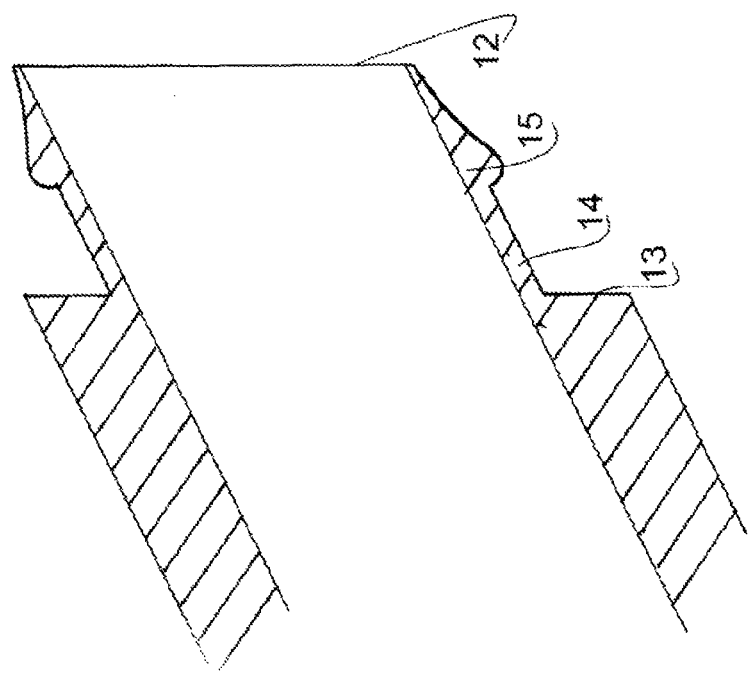
Figure 2:
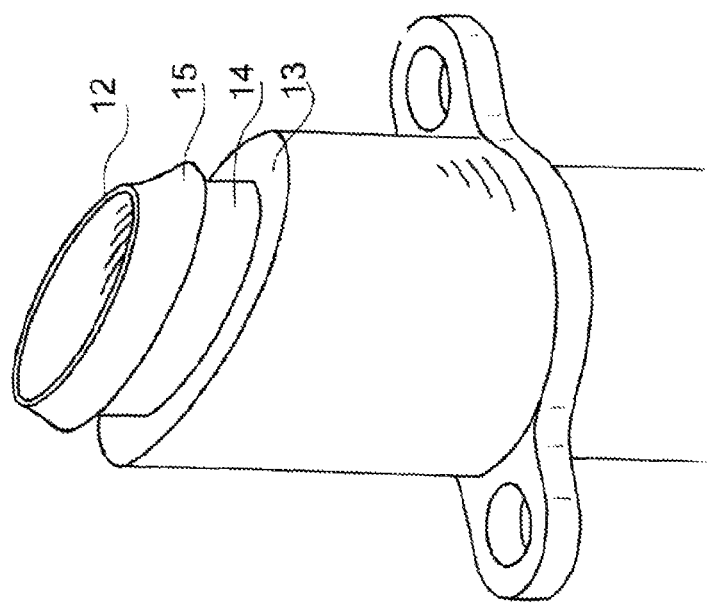
Figure 21:
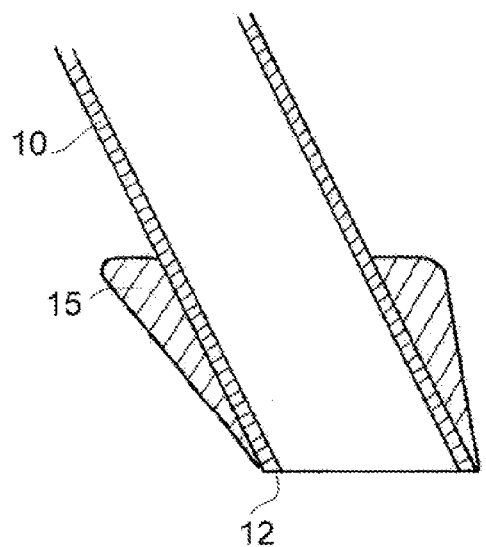
Figure 22:
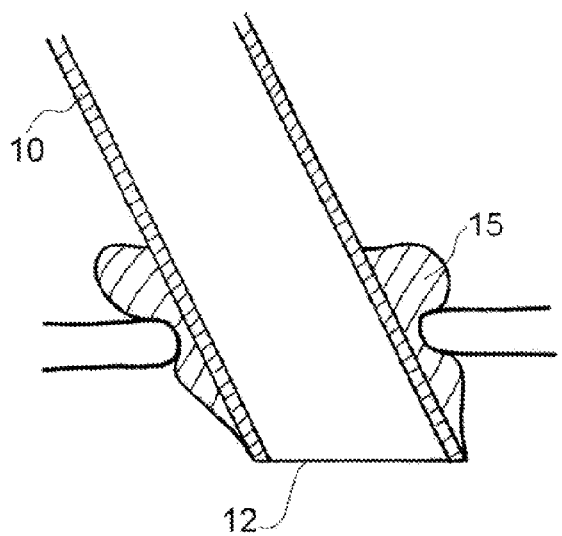
Figure 23:
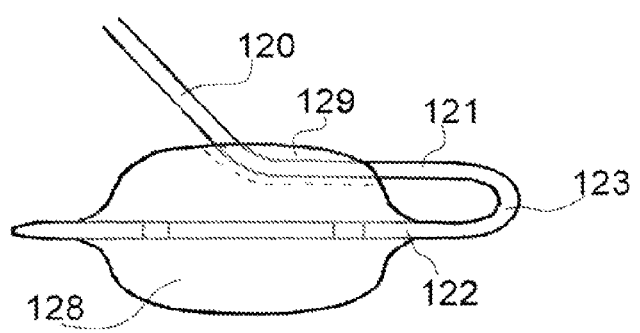
Figure 24:
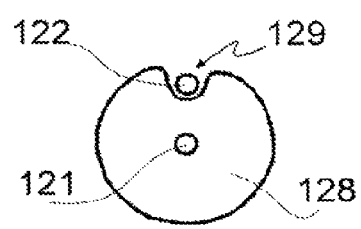
Figure 25:
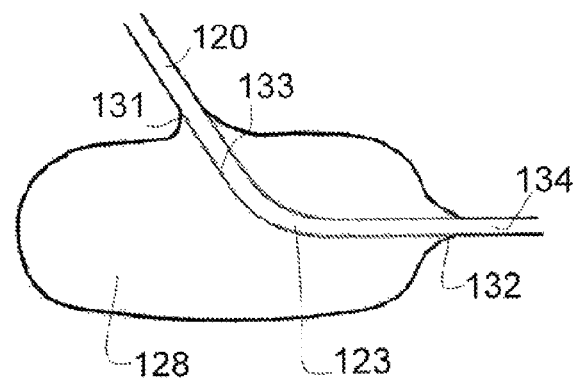

The present invention and its advantages will be better understood in the light of the following detailed description and the drawings enclosed with the presents on which:

FIG. 1 shows the various catheters and a pusher device used to insert an implant device according to the invention into the interior of a blood vessel, FIGS. 2 and 3 show respectively perspectives and longitudinal views of the distal end of a specific example of an introduction catheter, FIGS. 4 to 19 illustrate the various stages in the implanting of a prosthesis according to an example of the invention, FIG. 20 illustrates an implant device according to an example of the invention, FIGS. 21 and 22 illustrate a specific example of introduction catheter in two different configurations, FIGS. 23 and 24 show respectively a longitudinal view and a transverse view of a particular example of the invention, FIG. 25 shows a longitudinal view of another particular example of the invention, FIG. 26 shows three transverse views of an example of dilation catheter according to the invention, each of the views being taken in a different section of the catheter.

DETAILED DESCRIPTION OF THE INVENTION

A first example of an implant system according to the invention will now be described by reference to FIG. 1. In this example, the implant device includes an introduction catheter 10, means of penetration 20, a delivery catheter 30, a pusher device 40 and an implant device contained in the delivery catheter.

The introduction catheter 10 consists of a tubular body between a proximal end 11 and a distal end 12. The distal end 12 is designed to be introduced into the blood vessel 1 through a transparietal opening created by puncturing blood vessel 1.

Advantageously, the proximal end 11 is fitted with a haemostatic valve and an entry with a Luer lock allowing the injection of a product such as serum heparin.

The distal end 12 is bevelled for better penetration into the implant site. At the end of the distal end 12, the introduction catheter 10 has seal and stabilization means 16 fitting onto blood vessel 1. These seal and stabilization means 16 are designed to be withdrawn from the blood vessel 1 once the prosthesis 110 has been implanted. They are used to position, hold, and ensure the absence of leaks from, the introduction catheter 10 compared to blood vessel 1.

According to a preferred method, they include boss 13 a few millimeters above distal end 12 of introduction catheter 10. Boss 13 is positioned in such a way as to act as a stop between blood vessel 1 and introduction catheter 10 when introducing the catheter into vessel 1. Thus the movement of the introduction catheter 10 through blood vessel 1 is stopped when boss 13 comes into contact with the edge of the transparietal opening. The position of boss 13 compared to the distal end 12 of the introduction catheter 10 determines the length of the introduction catheter 10, which can penetrate blood vessel 1. The use of boss 13 as a stop on blood vessel 1 also enables the introduction catheter 10 to be accurately positioned.

Advantageously, the distal end of boss 13 lies within a plane parallel to the plane defined by the section of the distal end 12 on the bevelled introduction catheter 10. This configuration of boss 13 makes it possible to improve penetration and flexibility of use while maintaining introduction catheter 10 in position on blood vessel 1.

Preferentially, the seal and stabilization means 16 include a recess 14 adjacent to boss 13 and located between the latter and distal end 12 of introduction catheter 10. Recess 14 also lies in a plane parallel to the plane defined by the section of distal end 12 of the bevelled introduction catheter 10. Recess 14 is positioned in such a way as to fit with the edge of the transparietal opening in blood vessel 1. Blood vessel 1 has a certain elasticity and the penetration of introduction catheter 10 through the transparietal opening generates substantially radial constraints on the edge of the opening. These constraints decrease when the edge lodges in recess 14 since the diameter of introduction catheter 10 is narrower at recess 14 than between recess 14 and distal end 12 of introduction catheter 10.

Once lodged in recess 14, the edge is then stable and balanced, helping to maintain the connection between introduction catheter 10 and blood vessel 1.

Thus the combination of boss 13 and recess 14 ensures the correct placement and the maintenance of introduction catheter 10 in a particularly stable position on blood vessel 1. In addition, the combination ensures an effective seal between the edge of the transparietal opening and introduction catheter 10.

Moreover, the placement, maintenance and seal are particularly easy and fast procedures for the surgeon. The insertion of the edging in recess 14 is completed almost automatically and instantaneously when boss 13 touches the external wall of blood vessel 1.

The seal and stabilization means 16 do not require the displacement of any movable organ nor the filling of a hydraulic circuit. They are built in a single piece as part of introduction catheter 10 and are particularly strong. It is particularly important to guarantee a reliable seal between introduction catheter 10 and blood vessel 1. The stronger and simpler the seal means are to use, the better the reliability of the seal when implanting prosthesis 110.

Introduction catheter 10 is particularly easy and cheap to manufacture. Boss 13 and recess 14 can, for example, be formed from the same material or moulded or overmoulded and added onto introduction catheter 10.

From now on, we shall refer to the vascular prosthesis/stent assembly as "the implant".

The seal and stabilization means on introduction catheter 10 help, like the implant device described below, to significantly improve the rapidity and simplicity of known implant processes. However, the use of these seal and stabilization means on the one hand and the implant device on the other are perfectly independent of each other.

In particular, it is possible to change the structure of seal and stabilization means 16.

According to the design variations, these means include no fixed or non-deformable boss 13 or recess 14. Instead, they comprise a component made of shape-memory material, elastomer or an inflatable balloon or a combination of such components and such a balloon.

The component or balloon provide a controlled means of creating a boss 13 and/or a recess 14 so that, when introduction catheter 10 penetrates blood vessel 1, the component and/or balloon change shape and grasp the wall of the edge of the transparietal opening. This gives stability and a seal between introduction catheter 10 and the artery.

According to a specific example of introduction catheter 10, the catheter comprises penetration means at its distal end 12. These penetration means dilate the puncture opening. They are shaped like a cone 20.

They stretch substantially in a longitudinal direction along the tubular body and, advantageously, are flexible. The penetration means have a distal end 22 and a proximal end 21. They include a cylindrical tubular portion extending from proximal end 21 towards distal end 22 and a conical portion stretching from the distal end to the cylindrical portion. Thus distal end 22 substantially forms the tip of a cone and the conical portion flares out until the cylindrical portion. They are conformed so that the tip of the cone is introduced into proximal end 11 of introduction catheter 10 and slide along the tubular body to beyond distal end 12 of introduction catheter 10. The external diameter of the distal end is conformed so that the penetration means can be easily introduced into the lumen of blood vessel 1. The diameter of proximal end 21 on the penetration means is conformed to stop penetration means sliding inside introduction catheter 10 when said means exceed distal end 12 of introduction catheter 10 by a given distance.

The penetration means are positioned in such a way as to widen the diameter of the transparietal opening as they are being introduced into blood vessel 1. They therefore make it easier to introduce and position distal end 12 of introduction catheter 10 in blood vessel 1.

Moreover, the penetration means have a lumen from one side to the other, stretching from proximal end 21 to distal end 22. The lumen is designed as housing for at least one wire guide along which penetration means can be slid.

Advantageously, introduction catheter 10 has a profiled section 15 which flares out from distal end 12 to proximal end 11. Profiled section 15 may, for example, have a substantially conical and/or bevelled form. It may also have a bend with a variable gradient, as illustrated in the embodiment in FIGS. 2 and 3. It is positioned to facilitate the insertion of introduction catheter 10 in blood vessel 1 through the transparietal opening.

Advantageously, profiled section 15 stretches from distal end 12 to recess 14. It also has a rounded section at its junction with recess 14 to provide continuous gradual guidance round the edge of the transparietal opening from distal end 12 to recess 14.

It is located in the extension of the body of introduction catheter 10. It has a gradient greater than that of cone 20. Preferentially, this gradient is greater than the gradient of cone 20 by 10 to 70 degrees.

In the specific design shown in detail in FIGS. 21 and 22, profiled material 15 consists partly or wholly of a flexible elastic material such as silicon or any other biocompatible elastomer. On FIG. 21, profile shape 15 is in its standby position. On FIG. 22, distal end 12 of introduction catheter 10 is inserted into the wall of blood vessel 1. The profiled material then changes its form and follows the shape of the opening in the blood vessel.

The layout and material of profile 15 help to improve the placement of introduction catheter 10 on blood vessel 1. They also allow for the adaptation of distal end 12 of introduction catheter 10 to the edges of the transparietal opening.

Profile 15 therefore significantly improves the seal and the connection between introduction catheter 10 and blood vessel 1.

Profile 15 on distal end 12 of introduction catheter 10 also facilitates and simplifies the implanting of prosthesis 110. Technically, profile 15 is totally independent of the seal and stabilization means previously described and of dilation catheter 120 which will be detailed below.

The implant system also comprises a delivery catheter 30 that can be inserted into introduction catheter 10. Delivery catheter 30 has a proximal end 31, a distal end 32 and a tubular body stretching between proximal end 31 and distal end 32.

The external sections of distal end 32 and the tubular body of delivery catheter 30 are positioned so that the catheter can slide into the body of introduction catheter 10 when introduced by its proximal end 11.

Advantageously, the radial play between delivery catheter 30 and introduction catheter 10 is sufficiently slight to allow accurate guidance of delivery catheter 30 when it is slid into the body of introduction catheter 10.

Close to its proximal tip, delivery catheter 30 has a stop 33 designed to cooperate with proximal end 11 of introduction catheter 10 to stop delivery catheter 30 sliding towards distal end 12 of introduction catheter 10. The implant system is positioned in such a way that, when stop 33 comes into contact with proximal end 11 of introduction catheter 10, the distal ends of the introduction and delivery catheters are substantially positioned opposite one another.

Delivery catheter 30 has a lumen stretching from its proximal end 31 to its distal end 32. The lumen is positioned in such a way as to accommodate an implant device. The distal end of the delivery catheter is bevelled in the same way as the introduction catheter, on which it can be aligned thanks to markers or angular stops. Moreover, the system includes a pusher device 40 that ejects the implant device out of the delivery catheter by pushing it, at least partially, beyond distal end 32 of delivery catheter 30 and introduction catheter 10. Once pushed, the implant device can be positioned, at least partly, in blood vessel 1. To this end, pusher device 40 consists of a proximal end 41 associated with grippers designed to be used by the surgeon. It also comprises a distal end 42 designed to be introduced into the body of delivery catheter 30 from its proximal end 31 until it touches the implant device. The length of the pusher device 40 is substantially greater than the length of delivery catheter 30 and introduction catheter 10.

Advantageously, pusher device 40 comprises means of adjustment used to control the distance over which the implant device is pushed out of delivery catheter 30. The adjustment means include stop 43 designed to touch proximal end 31 of delivery catheter 30. They also include a removable spacer or wedge 34, positioned between said stop 43 and proximal end 31 on delivery catheter 30.

The implant system comprises a vascular prosthesis 110 designed to be deployed once positioned in the blood vessel 1.

The vascular prosthesis 110 can be straight or bifurcated. It consists of a main trunk or body 111 designed to be positioned inside blood vessel 1 receiving the implant. It also includes, in the case of a bypass, one or more legs 112 whose upper end enters the main portion of prosthesis 110 while its lower end is designed to be fluidly connected to a portion of blood vessel 1 located below the implant area.

In the case of a stenotic blood vessel 1 bypass, prosthesis 110 is implanted so that the stenosis 2 is located between the upper and lower ends of each of the legs 112. This device enables the blood to flow down the legs 112 forming the bypass. It can also flow through the stenosis 2.

The connection between the lower end of the legs 112 and a blood vessel can be sutured, for example.

The implant device also comprises a stent 130 positioned inside vascular prosthesis 110. Using a known method, stent 130 can act as support for prosthesis 110 where blood vessel 1 has been punctured. Stent 130 also helps to provide a seal between vascular prosthesis 110 and blood vessel 1.

The implant stent may or may not be made of shape-memory material and it can be located inside the vascular prosthesis or be an integral part of it.

Advantageously, stent 130 is self-extendable, notably thanks to the type of material used. To this end, stent 130 may be made of a shape-memory alloy.

Stent 130 is connected to vascular prosthesis 110. After deploying stent 130, the part of prosthesis 110 introduced into blood vessel 1 is sandwiched and immobilised between the external wall of stent 130 and the internal wall of blood vessel 1. This creates a seal between the implant and the blood vessel.

The implant device also comprises a balloon 128 and a dilation catheter 120.

Before assembly in delivery catheter 30, dilation catheter 120 and balloon 128 are positioned in stent 130 which is then compressed and, according to a particular design, maintained by ties. These ties can be undone from the proximal end 31 of delivery catheter 30 to enable the deployment of the stent 130.

The function of balloon 128 is to dilate in order to press on the implant in blood vessel 1. Stent 130 can deploy fully and hold vascular prosthesis 110 firmly in contact with blood vessel 1, at the same time providing an efficient seal.

Dilation catheter 120 has a proximal end and a distal end 124 and a body stretching between the proximal end and the distal end 124.

Dilation catheter 120 has a distal part designed to penetrate blood vessel 1. This distal part includes a bend 123, an upstream portion 121 and a downstream portion 122. Upstream portion 121 is adjacent to bend 123 and positioned between the bend and the proximal end of dilation catheter 120. The downstream portion 122 is adjacent to bend 123 and positioned between the bend and distal end 124 of dilation catheter 120. The upstream portion 121 and downstream portion 122 are substantially rectilinear.

Balloon 128 is supported by downstream portion 122. Dilation catheter 120 has a channel supplying fluid to balloon 128. Advantageously it has a substantially longitudinal shape and it stretches along the downstream portion 122. Dilation catheter 120 passes through it from one side to the other.

Preferentially, balloon 128 is linked to dilation catheter 120 by the two connection points corresponding to the sites in which dilation catheter 120 passes through balloon 128. Balloon 128 is therefore particularly well secured on dilation catheter 120.

Bend 123 is positioned so that downstream portion 122 forms a return to upstream portion 121. Bend 123 is substantially U-shaped. The upper and downstream portions form an angle of between 0° and 45° and more particularly between 0° and 20°. Advantageously, the angle is close to 0° so that, in the standby position, the upper and downstream portions run in substantially parallel directions.

Dilation catheter 120 is positioned so that, when it is placed in introduction catheter 10, downstream portion 122 is substantially folded along upstream portion 121. The downstream 121 and upstream 122 portions substantially run in the same longitudinal direction as introduction catheter 10. They are positioned side by side. Bend 123 is then positioned below downstream 121 and upstream 122 portions of introduction catheter 10. When the device is inside introduction catheter 10, balloon 128, supported by downstream portion 122, runs along beside upstream portion 121.

Optionally, in a dilated configuration, balloon 128 marks out a groove 129. Groove 129 is illustrated on the implant devices shown in FIGS. 23 and 24. Balloon 128 is positioned so that groove 129 is opposite upstream portion 121 and substantially parallel to it. Moreover, groove 129 is conformed and able to contain upstream portion 121 when the balloon dilates. Thus groove 129 is long enough to hold the entire upstream portion in contact with the balloon. It stretches over substantially one-half of the length of the balloon. The depth of groove 129 is calculated in such a way that upstream portion 121 does not project beyond the external casing of the balloon. Groove 129 is sufficiently wide to ensure that upstream portion 121 can be automatically inserted in groove 129 when balloon 128 is dilated.

Advantageously, groove 129 frees the implant device of any projection that might deform the wall of the blood vessel when the balloon is dilated. The implant device therefore perfectly follows the internal wall of the blood vessel.

Dilation catheter 120 is flexible, especially at bend 123.

When the distal part is introduced into blood vessel 1 by the transparietal route, the upper and downstream portions which bear the full weight of the balloon, turn in directions substantially parallel to the main direction 3 of blood vessel 1. The main direction 3 is then defined as the direction followed by the blood flowing into blood vessel 1.

The flexibility of dilation catheter 120 and the bevelled slope of distal end 12 of introduction catheter 10 help to ensure that upstream portion 121 is following the main direction 3 of blood vessel 1.

Dilation catheter 120 is positioned in such a way as to ensure that its proximal end projects beyond the introduction and delivery catheters.

The upstream portion and downstream portion of dilation catheter 120 are shaped such that, by a simple backward movement into the introduction catheter over a predetermined distance, balloon 128 is positioned substantially perpendicular to the transparietal opening through which introduction catheter 10 is inserted into blood vessel 1. More precisely, the centre of balloon 128 is located perpendicular to the transparietal opening.

Thus balloon 128 can follow the shape of the internal wall of blood vessel 1 over a sufficiently long distance to cover the entire length of the internal walls of vascular prosthesis 110 and stent 130. The length of balloon 128 can be adapted to be in contact with stent 130 along its entire length.

Advantageously, balloon 128 stretches substantially over the entire length of downstream portion 122. The downstream portion alone supports the balloon.

Dilation catheter 120 also comprises an initial lumen 141 able to hold an initial wire guide 5. The first wire guide 5 has a proximal end and a distal end. The first lumen stretches from the proximal end of dilation catheter 120 to an opening 126 on a level with bend 123. Opening 126 is located in the convex part so as to be in line with the lumen in upstream portion 121. This first lumen 141 is substantially rectilinear. Dilation catheter 120 can slide along first wire guide 5 which therefore acts as a guide for dilation catheter 120. The proximal end of first wire guide 5 is designed to project beyond the proximal end of dilation catheter 120. The distal end of first wire guide 5 is designed to project beyond opening 126. Thus when the distal part of dilation catheter 120 is introduced into blood vessel 1 and the convex part of bend 123 is oriented towards the upper section of blood vessel 1, the wire guide projects from dilation catheter 120 towards the upper section of blood vessel 1.

When first wire guide 5 is held in position at its proximal end and the surgeon pulls or pushes the proximal end of dilation catheter 120 towards the transparietal opening, the distal part of dilation catheter 120 can slide along this first wire guide towards its proximal or distal end in blood vessel 1. Dilation catheter 120 according to the invention enables a particularly accurate and simple placement along the blood vessel 1. Thus the invention significantly improves the accuracy of the placement of the implant device. Stent 130 and prosthesis 110 are consequently better positioned compared to blood vessel 1. The stability and the seal between prosthesis 110 and blood vessel 1 are stronger. The invention also reduces the time taken for prosthesis implant operations.

Preferentially dilation catheter 120 is sufficiently flexible to change its shape so that the lower part can be constrained into position substantially beyond the upper part. Advantageously, this flexibility in bend 123 facilitates the approximate alignment of upstream and downstream portions 121 and 122.

Dilation catheter 120 includes a second lumen 142 able to hold a second wire guide 6. This second lumen runs from the proximal end to distal end 124 of dilation catheter 120. Dilation catheter 120 is positioned to slide along second wire guide 6 which therefore functions as a wire guide for dilation catheter 120. Second wire guide 6 may, for example, be of a flexible type.

Second wire guide 6 has a proximal end designed to project beyond the proximal end of dilation catheter 120. The distal end of the second wire guide 6 projects through distal end 124 of dilation catheter 120. Thus when the distal part of dilation catheter 120 is introduced into blood vessel 1 and the convex part of bend 123 is oriented towards the upper section of blood vessel 1, the second wire guide projects beyond dilation catheter 120 towards the lower section of blood vessel 1. When second wire guide 6 is held at its proximal end and the surgeon pulls or pushes the proximal end of dilation catheter 120 towards the transparietal opening, the distal part of the catheter can then slide along wire guide 6 in blood vessel 1 and respectively towards the lower or upper section of the blood vessel.

Therefore, when the surgeon pushes on dilation catheter 120, it displaces the downstream portion 122 of dilation catheter 120 along blood vessel 1 and respectively towards its upper section, by sliding along first wire guide 5 and second wire guide 6.

Likewise, when the surgeon pulls on dilation catheter 120, it displaces downstream portion 122 of dilation catheter 120 along blood vessel 1 and respectively towards its lower section, by sliding along first wire guide 5 and second wire guide 6.

The use of two distinct wire guides 5 and 6, located respectively above and below the puncture, makes it possible to adjust the position of the implant in a particularly accurate manner, both above and below the puncture. It also improves guide security.

Moreover the presence of two wire guides provides better control of the positioning of the bend and the distal end of the dilation catheter within the blood vessel. This significantly reduces the risk of the bend or the distal end of the dilation catheter positioning itself between the internal wall of the blood vessel and any atheroma in the wall.

The flexibility of bend 123 makes it possible to withdraw dilation catheter 120 from blood vessel 1 by sliding it in introduction catheter 10 when the surgeon pulls on the proximal end of dilation catheter 120. More precisely, when dilation catheter 120 is pulled towards its proximal end, it slides along first 5 and/or second 6 wire guide, causing upstream portion 121 to move back into introduction catheter 10 as far as bend 123. Bend 123 changes shape and opens until downstream portion 122 aligns approximately with introduction catheter 10 so that it can slide within it. The invention therefore allows for the particularly simple, efficient and safe withdrawal of dilation catheter 120 after implanting prosthesis 110.

Moreover, the flexibility of dilation catheter 120 allows downstream portion 122 to be brought sufficiently close to upstream portion 121 so that balloon 128, in its non-deployed position, can be simultaneously in contact with upstream portion 121 and downstream portion 122. Thus the flexibility of bend 123 allows dilation catheter 120 to be folded over, thereby considerably reducing the space it occupies. Dilation catheter 120 can therefore be introduced in conventional small delivery catheters.

Advantageously, in addition to being easily flexible, dilation catheter 120 has very good elasticity. Therefore as soon as it is removed from delivery catheter 30, it is no longer compressed and it automatically returns to its standby configuration.

The invention therefore requires no specific mechanism to open dilation catheter 120 at an angle when its distal end is removed from delivery catheter 30.

Likewise the elasticity enables upstream portion 121 to retain a substantially rectilinear shape after its shape has been changed at distal end 12 of introduction catheter 10.

Moreover, the elasticity enables the distal part of dilation catheter 120 to be oriented approximately in the direction of blood flow.

FIG. 26A shows a transverse section of catheter 120 seen above bend 123. Catheter 120 has a substantially circular structure. It includes a lumen 140 through which dilation fluid passes, a lumen 141 through which first wire guide 5 passes and a lumen 142 through which second wire guide 6 passes. Lumen 142, which allows for the passage of second wire guide 6, is located in the centre of catheter 120. Lumen 140, which allows for the passage of dilation fluid, is located concentrically compared to lumen 142 through which second wire guide 6 passes. Lumen 141 through which the first wire guide passes is located between lumen 140 that allows the flow of dilation fluid and the outer edge of catheter 120.

FIG. 26B shows a transverse section of catheter 120 seen below bend 123 within balloon 128. The catheter's diameter is smaller since it does not need to accommodate lumen 141 through which first wire guide 5 passes. All that remain are lumina 140 and 142.

FIG. 26C shows a transverse section of catheter 120 through a section located below the opening through which the dilation fluid enters the balloon to deploy it. In this section, dilation catheter 120 therefore shows only lumen 142 providing access for second wire guide 6.

As a non-restrictive example, an implant system according to an embodiment of the invention will now be described in detail.

Introduction catheter 10 has an external diameter of 12 millimeters and an internal diameter of 10.6 millimeters. Distal end 12 of introduction catheter 10 is bevelled at a 30° angle. Recess 14 is located 3 millimeters from this same distal end. Recess 14 is 3 millimeters in length along the longitudinal direction of introduction catheter 10 and 0.3 millimeters deep. Boss 13 has a height of 3 millimeters and is located at 6 millimeters from distal end 12 of introduction catheter 10.

Delivery catheter 30 has an external diameter of approximately 10.5 millimeters.

Stent 130 is self-extending and made of shape-memory alloy or is inflatable by balloon. It has a length of approximately 30 millimeters. Stent 130 can be compressed and kept to a diameter of less than 6 millimeters by ties. It has a length of between 32 and 34 mm.

Prosthesis 110 consists typically of a body 111 of between 14 and 24 millimeters depending on the diameter of blood vessel 1, an initial bypass with a diameter of 10 to 20 millimeters and legs 112 with diameters of 5 to 10

The useful length of a balloon, i.e. the length of the portion in which the implant is inserted in the blood vessel is greater than the length of the stent. The diameter of the deployed balloon is substantially identical to the diameter of the stent. As a non-restrictive example, the balloon is made of silicon, polyethylene, polyurethane, latex or with by-products of these materials.

The various stages in an implant procedure using prosthesis 110 according to the invention will be detailed by reference to FIGS. 4 to 20. Serum heparin is injected into introduction catheter 10 before use and at various stages in the implant protocol as preferred by the clinician.

In this example, prosthesis 110 is designed to provide a bypass at the level of stenosis 2 present in artery.

As shown on FIG. 4, the artery is punctured using a needle 4. This puncture then creates a transparietal opening above the artery. Needle 4 includes a lumen and a first wire guide 5 of the "stiff guide" type, which is introduced into the artery by the lumen of needle 4 (FIG. 5). Needle 4 is then withdrawn and first wire guide 5 remains in position (FIG. 6). The proximal end of first wire guide 5 is then inserted in the distal end of cone 22 of introduction catheter 10. Cone 20 of introduction catheter 10 is then brought into contact with the blood vessel by sliding it along first wire guide 5. Cone 20 of introduction catheter 10 penetrates the wall of blood vessel 1 by sliding along first wire guide 5, widening the diameter of the transparietal opening (FIG. 7). Distal end 12 of introduction catheter 10 is also inserted into blood vessel 1 until its boss 13 is stopped by the outer wall of the blood vessel. The edge of the transparietal opening then fits into recess 14 of introduction catheter 10 (FIG. 8). The placement and maintenance of, and seal between, introduction catheter 10 and the blood vessel are then complete.

Cone 20 is then withdrawn from introduction catheter 10 through the haemostatic valve and along the wire guide which remains in position (FIG. 9). Serum heparin is injected into introduction catheter 10 (FIG. 10).

Delivery catheter 30, pusher device 40 and the implant are previously wetted with serum heparin. The proximal end of first wire guide 5, which projects beyond proximal end 11 of introduction catheter 10 is introduced into opening 126 of dilation catheter 120 located on a level with bend 123. Opening 126 is accessible from the distal end of delivery catheter 30. Delivery catheter 30 is inserted into introduction catheter 10 (FIGS. 11 and 12) and advanced until its stop 33 touches proximal end 11 of introduction catheter 10. The bent tip of dilation catheter 120 then protrudes slightly into the artery (FIG. 13A).

Wedge 34 blocking pusher device 40 in delivery catheter 30 is withdrawn (FIGS. 13B and 13C). Pusher device 40 is advanced into delivery catheter 30 until stop 43 of the pusher touches proximal end 31 of delivery catheter 30. The purpose of wedge 34 is clearly illustrated in FIGS. 13A to 14.

The implant device is advanced along first wire guide 5 by pusher device 40. This advances body 111 of prosthesis 110 in blood vessel 1 so that body 111 of prosthesis 110 and balloon 128 penetrate the artery.

Downstream portion 122 is rotated and released. The opening may require the prior opening of a tie. Stent 130 is then positioned approximately in the same direction as the blood flow i.e. along the main axis of the blood vessel (FIG. 14).

Under x-ray control, delivery catheter 30 is withdrawn towards the rear of introduction catheter 10. The withdrawal may, for example, occur over a distance of 12 millimeters and be monitored by a visual marker on the tubular proximal part of delivery catheter 30. This brings the part of the implant containing stent 130 up against distal end 12 of introduction catheter 10 (FIG. 15). Stent 130 is then positioned under and across distal end 12 of introduction catheter 10. X-ray is used to check that stent 130 is correctly positioned.

Also under x-ray control, stent 130 is deployed by releasing the ties and/or by inflating the balloon. The implant device is then no longer mechanically linked to the pusher device. By pushing or pulling the proximal end of dilation catheter 120 towards the transparietal opening, balloon 128 can be displaced in main direction 3 of the artery and towards the upper and lower sections of artery by sliding along first wire guide 5 or second wire guide 6 (FIG. 16).

Under x-ray control, balloon 128 is inflated. This pushes on the implant in the blood vessel and pushes distal end 12 of introduction catheter 10 outside the artery (FIG. 17). From then on, the implant provides a seal between vascular prosthesis 110 and the artery. The placement of the balloon in main direction 3 can again be adjusted by pushing or pulling the proximal end of dilation catheter 120 to slide balloon 128 along first wire guide 5 or second wire guide 6 and upwards or downwards.

The new placement of the balloon, followed by further inflation of the balloon, can optimise the contact of the implant in the blood vessel, thereby improving the seal.

Introduction catheter 10, delivery catheter 30 and the pusher device are then removed from the patient.

Balloon 128 is then deflated (FIG. 18). The seal round the connection between the implant device and the blood vessel is checked. If it is not satisfactory, balloon 128 can be re-inflated for a further attempt. If the problem persists, a clamp prepositioned higher up will stop blood circulation above the puncture in the blood vessel and a conventional bypass can be done.

Once the seal between the implant device and the blood vessel is satisfactory, dilation catheter 120 is withdrawn by pulling its proximal end. Dilation catheter 120 slides along first wire guide 5 as it is being withdrawn. First wire guide 5 is then withdrawn through the lumen of prosthesis 110 (FIG. 19).

The insertion of the implant is complete and the bypass can be finished in the conventional manner.

The above example of a procedure describes an implant system comprising a first wire guide 5 running through the blood vessel above the puncture and a second wire guide 6 running through the blood vessel below the puncture. It is, of course, possible to place the first wire guide 5 below the puncture and the second wire guide 6 above.

Moreover, in another embodiment, the implant system may have only one lumen and a single wire guide. The wire runs through the blood vessel above or below the puncture and, with the single lumen, fulfils the same function as the lumina and guides described above i.e. it slides the distal end of the dilation catheter towards the lower or upper section of the blood vessel to adjust the position of the implant.

A variation of dilation catheter 120 according to the invention will now be described by reference to FIG. 20.

The implant device has an elongated tip 125 on a level with bend 123, extending dilation catheter 120. Elongated tip 125 has a substantially truncated configuration. It comprises one obtuse-angled extremity 127 and one flared extremity. The diameter of tip 125 narrows beyond bend 123 and flares out from bend 123 to distal end 124 of dilation catheter 120. Tip 125 encases bend 123. It has a lumen coinciding with opening 126 so that the first lumen of dilation catheter 120 coincides with the lumen of tip 125. Thus first wire guide 5 provides a guide along which dilation catheter 120 and tip 125 can slide.

As a non-restrictive example, the length of the obtuse-angled tip is between 3 and 12 cm. The obtuse-angled tip has a gradient of between 5° and 25°. The tip is made of plastic. Advantageously, the angle at the top of the cone lies between 10° and 50°.

This example doe not require the use of cone 20 or delivery catheter 30 described in the previous example.

Tip 125 acts as a penetration mean. It projects beyond distal end 12 of introduction catheter 10 and is guided by first wire guide 5 to the puncture in the wall of the blood vessel 1. It penetrates through this puncture and widens its diameter. It enables the edge of the transparietal opening to fit into the seal and stabilization means 16 of introduction catheter 10. Since tip 125 acts as a penetration mean like introduction catheter 10, there is no need for the stage consisting of inserting a cone 20 into introduction catheter 10 and removing it at a later stage. Such a dilation catheter 120 therefore simplifies the conventional procedures used to implant prosthesis 110.

Moreover, such a dilation catheter 120 is fitted into a delivery catheter 30 which can be inserted in introduction catheter 10 at the start of the operation. This significantly reduces the number of stages and the duration of the usual implant procedures.

Also, tip 125 remains constantly in front of prosthesis 110 and stent 130 when they are inserted in the blood vessel 1. It therefore helps to provide effective protection and ensures the integrity of the implant and blood vessel 1.

Preferentially, distal end 124 of dilation catheter 120 should comprise a second tip, again substantially truncated in form. Second tip has an obtuse-angled tip 127 extending distal end 124 of dilation catheter 120 and a flared end increasing its diameter from distal end 124 of dilation catheter 120 to bend 123. The flared ends of the two tips 125 are positioned opposite each other.

Alternatively, the obtuse-angled end 127 of each tip 125 may be spherical rather than conical. The spherical shape has substantially the same advantages as the conical form described above.

In particular, second tip protects stent 130, prosthesis 110 and blood vessel 1 when the implant device is withdrawn.

Tips 125 may be substantially rigid. To this end, prosthesis 110 has an opening in the part of the bypass before the bifurcation to allow for the withdrawal of dilation catheter 120. Once prosthesis 110 has been put in position, the bypass can be clamped just above the artery. The blood circulation is not then stopped in the patient's vascular system and the surgeon can suture the opening. Preferentially, the opening can have a loose suture, an enclosure or any other system that instantly closes the opening when balloon 128 is withdrawn.

In another embodiment, tips 125 are positioned so that their section can be reduced in a controlled manner on a plane substantially perpendicular to the longitudinal direction of downstream portion 122. The reduced diameter allows dilation catheter 120 to be withdrawn through the channels formed by legs 112 of prosthesis 110 without the need for an opening in the prosthesis.

The reduction in diameter can be achieved by mechanical traction. It can also be achieved by removing the fluid supplying tips 125. To this end, dilation catheter 120 comprises a duct positioned in such a way as to provide fluid to each of the profiled tips 125, thereby creating variable diameters for the tips as required, depending on the supply or removal of the fluid.

As a non-restrictive example, a procedure to implant vascular prosthesis 110 carried out using an implant device as shown in FIG. 20 may include the following stages:

blood vessel 1 in which the prosthesis is to be implanted is punctured with a needle 4.

a first wire guide 5 is inserted through needle 4 and the needle is withdrawn.

an introduction catheter 10 is slipped along the first wire guide 5. Tip 125 projects beyond the distal end of the catheter, encasing bend 123 of dilation catheter 120 placed in introduction catheter 10.

tip 125 penetrates the puncture from its obtuse-angled end 127 and widens the diameter of the puncture as it is inserted.

tip 125 is inserted in blood vessel 1 until distal end 12 of introduction catheter 10 penetrates the vessel and seal and stabilization means 16 fit with the edge of the transparietal opening.

tip 125 and the distal part of dilation catheter 120 are inserted in blood vessel 1 by pushing the implant device towards distal end 32 of introduction catheter 10.

the following stages are similar to the ones described for a procedure using the implant device described above and illustrated in FIGS. 4 to 19. The upper 11 and lower 12 portions of introduction catheter 10 are rotated and released.

the downstream portion 122 is naturally oriented in the direction of blood flow.

the position of dilation catheter 120 is adjusted above or below blood vessel 1 by sliding it respectively along first wire guide 5 or second wire guide 6.

balloon 128 is inflated to press on the implant in the blood vessel.

balloon 128 is deflated and removed, with dilation catheter 120, from introduction catheter 10.

introduction catheter 10 is removed.

According to a variation, the dilation catheter has a bend 123 housed inside a balloon 128 with a central, substantially cylindrical portion between two tips. The implant device is positioned so that a connection point 131 between balloon 128 and dilation catheter 120 is located substantially in the middle of the cylinder, and so that another connection point 132 between balloon 128 and dilation catheter 120 is located substantially at one of the tips of balloon 128.

Thus bend 123 is substantially L-shaped. More generally, portions 133 and 134 adjacent to bend 123 form an angle of between 130° and 60° and more particularly an angle of between 120° and 90°.

The portion of dilation catheter located between the bend and the distal end of the dilation catheter is designated as downstream portion 134. The portion of dilation catheter adjacent to bend 123 and located above the bend 123 is designated as upstream portion 133. Thus, balloon 128 is supported firstly by downstream portion 134 and secondly by upstream portion 133. It is therefore partially supported by downstream portion 134. The implant device is positioned in such a way that downstream portion 134 is substantially parallel to the blood vessel during the implant procedure.

Advantageously, balloon 128 runs substantially along the entire length of downstream portion 134.

The dilation catheter includes a lumen through which a guide is passed from the proximal end to the distal end of the dilation catheter. The guide, like the first and second guides described in the previous examples, provides a guide when sliding the dilation catheter. For reasons of clarity, the guide is not shown on FIG. 25.

This variation reduces the size of the implant device and simplifies and increases the safety of the implant procedure. The portion of the dilation catheter in which guide 2 circulates is no longer required. Its removal decreases the size of the device. It should be remembered that, in the previously described embodiments, one stage consisted of pushing the implant sufficiently far beyond the delivery catheter to insert the entire upstream and downstream portions of the dilation catheter into the blood vessel. A further removal stage is required to position the middle of the implant substantially perpendicular to the puncture. Because of the absence of the portion of the dilation catheter containing the lumen designed specifically for the second wire guide, the dilation catheter does not project as far beyond the lower tip of the implant. This reduces the amplitude of the movements required to insert the implant in the blood vessel and pull it back into position substantially perpendicular to the puncture. The reduced amplitude of movement limits the risks linked to the positioning of the implant in the blood vessel.

Such an implant device can, of course, be combined with the variations described above regarding the profiled tips.

The dimensions of the implant device will be easily adapted to suit the various diameters of blood vessels requiring an implant. It should be noted that, by improving the simplicity and safety of a prosthesis implant perpendicular to a puncture, the procedure is particularly advantageous for blood vessels with a small diameter or that are difficult to access through an intralumen opening.

The present invention offers several solutions including respectively a dilation catheter, seal and stabilization means on the introduction catheter and the distal end of the introduction catheter. Although technically independent, these methods each help to improve the accuracy and decrease the duration and difficulty of conventional vascular prosthesis implant procedures.

REFERENCES

1. Blood vessel
2. Stenosis
3. Main direction
4. Needle
5. First wire guide
6. Second we guide
10. Introduction catheter
11. Proximal end of the introduction catheter
12. Distal end of the introduction catheter
13. Boss
14. Recess
15. Profiled section
16. Seal and stabilization means
20. Cone
21. Proximal end of the cone
22. Distal end of the cone
30. Delivery catheter
31. Proximal end of the delivery catheter
32. Distal end of the delivery catheter
33. Stop on the delivery catheter
40. Pusher device
41. Proximal end of the pusher device
42. Distal end of the pusher device
43. Stop on the pusher device
34. Spacer or wedge
110. Prosthesis
111. Body
112. Leg
120. Dilation catheter
121. Upstream portion
122. Downstream portion
123. Bend or elbow
124. Distal end of the dilation catheter
125. Tip
126. Opening
127. Obtuse-angled tip
128. Balloon
129. Groove
130. Stent
131. First connection point
132. Second connection point
133. Upstream portion of the dilation catheter
134. Downstream portion of the dilation catheter
140. Lumen allowing the passage of dilation fluid
141. Lumen allowing the passage of the first wire guide
142. Lumen allowing the passage of the second wire guide

The invention claimed is:

1. A system to implant a vascular prosthesis (110) in a blood vessel (1) comprising:
   an implant device; and
   an introduction catheter (10) comprising a proximal end (11), a distal end (12), and a distal aperture at the distal end (12) of the introduction catheter (10), the implant device being designed to slide from the proximal end (11) to the distal end (12) of the introduction catheter (10),
   the implant device comprising
   i) a single balloon (128) and
   ii) a dilation catheter (120) arranged to supply fluid to the balloon (128),
   the dilation catheter (120) having a proximal end, a distal end (124), and a distal part designed to be introduced into the vessel (1),
   wherein the distal part of the dilation catheter (120) comprises a bend (123) and an upstream portion (121) and a downstream portion (122) that are contiguous to the bend (123), the bend of the dilation catheter (120) being arranged between the downstream and upstream portions (121, 122) of the dilation catheter (120) and, respectively, the proximal end and the distal end (124) of the dilation catheter (120), the balloon (128) being entirely supported by the downstream portion (122) of the dilation catheter (120),
   wherein the system is arranged so that when the dilation catheter (120) is placed in the introduction catheter (10), the downstream portion (122) of the dilation catheter (120) is being substantially folded along the upstream portion (121) of the dilation catheter (120) and the bend (123) of the dilation catheter (120) is being positioned below the downstream portion (122) and the upstream portion (121) of the dilatation catheter (120), thus facing the distal aperture of the introduction catheter (10), the configuration allowing thereby to introduce into a blood vessel, through a puncture, first the bend (123) of the dilatation catheter (120) and thereafter the balloon (128) entirely supported by the downstream portion (122) of the dilation catheter (120) and the distal end (124) of the dilatation catheter (120), and
   wherein the system being thereby configured to implant the vascular prosthesis perpendicular to a puncture in a vessel/artery, through which the prosthesis is to be inserted, while running in a direction parallel to the longitudinal axis of the blood vessel.

2. A system to implant a vascular prosthesis (110) according to claim 1, wherein the introduction catheter (10) further comprises a seal and stabilisation unit (16) positioned to provide a stable sealed connection between the introduction catheter (10) and the blood vessel (1).

3. A system to implant a vascular prosthesis (110) according to claim 2, wherein the seal and stabilisation unit includes a boss (13) and a recess (14) located between the boss (13) and the distal end (12) of the introduction catheter (10).

4. A system to implant a vascular prosthesis (110) according to claim 2, wherein the seal and stabilisation unit is (16) and positioned to match the walls of an approximately circular opening.

5. A system to implant a vascular prosthesis (110) according to claim 1, wherein,
the dilation catheter (120) includes a first lumen between its proximal end and the bend (123) into which a first wire guide (5) can be placed, and
the first lumen stretches from the proximal end of the dilation catheter (120) to an opening (126) of the dilation catheter (120), the opening (126) being located on the bend (123).

6. A system to implant a vascular prosthesis (110) according to claim 1, wherein the dilation catheter (120) has one of a cone-shaped and a spherical tip (125) that encases the bend (123).

7. A system to implant a vascular prosthesis (110) according to claim 6, wherein the tip (125) has a truncated configuration and presents a diameter that narrows beyond the bend (123) and that flares out from the bend (123) to the distal end (124) of the dilation catheter (120).

8. A system to implant a vascular prosthesis (110) according to claim 5, wherein,
the dilation catheter (120) has a cone-shaped tip (125) that encases the bend (123) and
the tip (125) has a lumen coinciding with the opening (126) so that the first lumen of the dilation catheter (120) coincides with the lumen of the tip (125), allowing thereby the dilation catheter (120) and the tip (125) to slide along the first wire guide (5).

9. A system to implant a vascular prosthesis (110) according to claim 1, further comprising:
a bifurcated prosthesis (110), wherein the prosthesis (110) comprises a main body (111) designed to be positioned inside the blood vessel (1) and at least one leg (112) having an upper end entering said body (111) and having a lower end designed to be fluidly connected to a portion of the blood vessel (1) located downstream the implant area, wherein the downstream portion (122) of the dilatation catheter (10) extends through the entire length of said body (111), the bend (123) and the distal end (124) being outside the prosthesis (110) and wherein the upstream portion passes through the at least one more leg (112).

10. A system to implant a vascular prosthesis (110) according to claim 1, wherein in a dilated configuration, the balloon (128) marks out a groove (129), the groove (129) being conformed to contain the upstream portion (121) when the balloon (128) dilates.

11. A system to implant a vascular prosthesis (110) according to claim 10, wherein,
the groove (129) is deep enough such that the upstream portion (121) does not project beyond an external casing of the balloon when the balloon is dilated, and
the groove (129) is long enough to hold the entire upstream portion (121) in contact with the balloon when the balloon is dilated and wherein the groove (129) is wide enough to ensure that the upstream portion (121) can be automatically inserted in the groove (129) when balloon (128) is dilated.

12. A system to implant a vascular prosthesis (110) according to claim 10, wherein the groove (129) is arranged to free the implant device of any projection that tends to deform the wall of the blood vessel (1) when the balloon (128) is dilated.

13. A system to implant a vascular prosthesis (110) according to claim 1, wherein the upstream (121) and downstream (122) portions form an angle of between 0° and 30° therebetween.

14. A system to implant a vascular prosthesis (110) according to claim 1, wherein the bend (123) is substantially U-shaped.

15. A system to implant a vascular prosthesis (110) according to claim 1, wherein the dilation catheter (120) is elastic at the bend (123) so that the upstream (121) and downstream (122) portions can be moved closer to, and further from, each other.

16. A system to implant a vascular prosthesis (110) according to claim 1, wherein the dilation catheter (120) includes a first lumen between its proximal end and the bend (123) into which a first wire guide (5) can be placed.

17. A system to implant a vascular prosthesis (110) according to claim 1, further comprising a second lumen between the proximal end and the distal end (124) of the dilation catheter (120), the second lumen being shaped and suitable for a second wire guide (6).

18. A system to implant a vascular prosthesis (110) according to claim 1, wherein one of the bend (123) and the distal end (124) of the dilation catheter (120) has a cone-shaped or spherical tip (125) extending the downstream portion (122).

19. A system to implant a vascular prosthesis (110) according to claim 1, further comprising the vascular prosthesis (110).

20. A system to implant a vascular prosthesis (110) in a blood vessel (1) comprising:
an implant device; and
an introduction catheter (10) comprising a proximal end (11), a distal end (12), and a distal aperture at the distal end (12) of the introduction catheter (10), the implant device slideable from the proximal end (11) to the distal end (12) of the introduction catheter (10),
the implant device comprising i) a single balloon (128) and ii) a dilation catheter (120) that supplies fluid to the balloon (128), the dilation catheter (120) having a proximal end, a distal end (124), and a distal part introduceable into the blood vessel (1),
wherein the distal part comprises a bend (123) and an upstream portion (121) and a downstream portion (122) that are contiguous to the bend (123), the bend being arranged between the downstream and upstream portions (121, 122) and, respectively, the proximal end and the distal end (124), the balloon (128) being entirely supported by the downstream portion (122),
wherein the system is arranged so that when the dilation catheter (120) is placed in the introduction catheter (10), the downstream portion (122) is being substantially folded along the upstream portion (121) and the bend (123) is being positioned below the downstream portion (122) and the upstream portion (121) of the dilatation catheter (120), thus facing the distal aperture of the introduction catheter (10), the configuration allowing thereby to introduce into a blood vessel, through a puncture, first the bend (123) of the dilatation catheter (120) and thereafter the balloon (128) entirely supported by the downstream portion (122) of the dilation catheter (120) and the distal end (124) of the dilatation catheter (120), and wherein the system thereby with the vascular prosthesis perpendicular to the puncture in the blood vessel, the prosthesis is insertable through the puncture, while running in a direction parallel to a longitudinal axis of the blood vessel.

* * * * *